US005700640A

United States Patent [19]
Voss et al.

[11] Patent Number: 5,700,640
[45] Date of Patent: Dec. 23, 1997

[54] INDUCERS OF GAMMA GLOBIN GENE EXPRESSION AND SCREENING ASSAYS THEREFOR

[75] Inventors: Jeffrey W. Voss, West Boylston; Connie Caron, Westborough, both of Mass.

[73] Assignee: BASF Aktiengesellschaft, Germany

[21] Appl. No.: 308,461

[22] Filed: Sep. 16, 1994

[51] Int. Cl.$^6$ .................................................. C12Q 1/68
[52] U.S. Cl. ........................... 435/6; 435/320.1; 435/372; 536/24.1
[58] Field of Search ................... 435/320.1, 6, 240.2, 435/372; 536/24.1

[56] References Cited

U.S. PATENT DOCUMENTS

| | | | |
|---|---|---|---|
| 4,699,926 | 10/1987 | Abraham et al. | 514/563 |
| 4,751,244 | 6/1988 | Abraham et al. | 514/563 |
| 4,822,821 | 4/1989 | Perrine | 514/557 |
| 4,997,815 | 3/1991 | Perrine et al. | 514/8 |
| 5,025,029 | 6/1991 | Perrine | 514/381 |
| 5,216,004 | 6/1993 | Perrine | 514/381 |

FOREIGN PATENT DOCUMENTS

| | | |
|---|---|---|
| 0 240 256 | 10/1987 | European Pat. Off. . |
| 0 617 966 A1 | 10/1994 | European Pat. Off. . |
| WO 92/04913 | 4/1992 | WIPO . |
| WO 93/18761 | 9/1993 | WIPO . |
| WO 95/11699 | 5/1995 | WIPO . |

OTHER PUBLICATIONS

Caterina, J.J. et al., "Cloning and Functional Characterization of LCR-F1: a bZIP Transcription Factor That Activates Erythroid-Specific, Human Globin Gene Expression", *Nucleic Acids Research* 22:12, 2383–2391 (1994).

Lloyd, J.A. et al., "Human γ–to β–Globin Gene Switching Using a Mini Construct in Transgenic Mice", *Mol. Cell. Biol.* 12:4, 1561–1567 (1992).

Perrine, S.P. et al., "Pharmacologic Prevention and Reversal of Globin Gene Switching", *Regul. Hemoglobin Switching, Proc. Conf. Hemoglobin Switching*, 7th (1991), Meeting Date 1990, 425–436.

Pondel, M.D. et al., "The Developmental Regulation of the Human ζ–globin Gene in Transgenic Mice Employing β–galactosidase as a Reporter Gene", *Nucleic Acids Research* 20:21, 5655–5660 (1992).

Wu, Y. et al., "Activation of Globin Gene Expression by cDNAs from Induced K562 Cells", *Journal of Bio. Chem.* 266:26, 17566–17572 (1991).

Adolf, G. and Swetly, P., "Interferon Production by Human Lymphoblastoid Cells is Stimulated by Inducers of Friend Cell Differentiation," *Virology (USA)*, vol. 99, No. 1, 158–166 (1979), International Search Report for PCT/US95/11823, issued Mar. 11, 1996.

Wu et al., *J. Biol. Chem.*, vol. 266, 1991, pp. 17566–17572.

Lumelsky et al., *Mol. Cell. Biol.*, vol. 11, 1991, pp. 3528–2536.

Constantoulakis et al., *Blood*, vol. 74, 1989, pp. 1963–1971.

Blau, C.A., et al., "Fetal Homoglobin Induction With Butyric Acid: Efficacy and Toxicity", Blood 81:529–537 (1993).

Bodine, D.M. and Ley, T.J., "An enhancer element lies 3'to the human $^A$γ globin gene", *EMBO J.* 6:2997–3004 (1987).

Constantoulakis, B., et al., "Locus Control Region–Aγ Transgenic Mice: A New Model for Studying the Induction of Fetal Hemoglobin in the Adult", *Blood* 77:1326–1333 (1991).

Fibach, E., et al., "Enhanced Fetal Hemoglobin Production by Phenylacetate and 4–Phenylbutyrate in Erythroid Precursors Derived From Normal Donors and Patients With Sickle Cell Anemia and β–Thalassemia", *Blood* 82:2203–2209 (1993).

Glauber, J., et al., "5'–Flanking Sequences Mediate Butyrate Stimulation of Embryonic Globin Gene Expression in Adult Erythroid Cells", *Mol. Cell. Biol.* 11:4690–4697 (1991).

Landau, H., et al., "Growth and Sexual Development Before and After Sex Steriod Therapy in Patients With Thalassemia Major", *Arch. Intern. Med.* 144:2341–2346 (1984).

Lavelle, D., et al., "Fetal Homoglobin Reactivation in Baboon and Man: A Short Perspective", *Am. J. Hematol.* 42:91–95 (1993).

Leder, A. and Leder, P., "Butyric Acid, a Potent Inducer of Erythroid Differentiation in Cultured Erythroleukemic Cells", *Cell* 5:319–322 (1975).

Mascolo, N., et al., "Mechanism of Short–Chain Fatty Acid Uptake by Apical Membrane Vesicles of Rat Distal Colon", *Gastroent.* 101:331–338 (1991).

Newmark, H., et al., "Butyrate as a differentiating agent: pharmacokinetics, analogues and current status", *Cancer Lett.* 78:1–5 (1994).

Perrine, S.P., et al., "Butyrate infusions in the ovine fetus delay the biologic clock for globin gene switching", *Proc. Natl. Acad. Sci. USA* 85:8540–8542 (1988).

(List continued on next page.)

*Primary Examiner*—James Ketter
*Attorney, Agent, or Firm*—Lahive & Cockfield, LLP; Giulio A. DeConti, Jr.; Catherine J. Kara

[57] ABSTRACT

Methods for stimulating gamma globin gene expression in a mammalian cell comprising contacting the cell with a compound selected from valeric acid and certain isomers, derivatives or salts thereof, including isovaleric acid, 4-pentynoic acid and methylthioacetic acid, or an inhibitor of a short chain fatty acyl CoA dehydrogenase, or an activator of protein kinase C are disclosed. The methods of the invention are particularly useful for ameliorating β-globin disorders, such as sickle cell anemia or β-thalassemia. The method of the invention can also be used to prevent or ameliorate malaria in a mammal. The compounds of the invention can also be used to stimulate differentiation of a cell. Pharmaceutical compositions of the active compounds of the invention are also disclosed. Screening assays for identifying agents that stimulate gamma globin gene expression in an erythroid cell, stimulate cell differentiation or stimulate transport of a short chain fatty acid, or derivative or salt thereof, into cells are also disclosed.

37 Claims, 17 Drawing Sheets

OTHER PUBLICATIONS

Perrine, S.P., et al., "Butyric Acid Analogues Augment γ Globin Gene Expression in Neonatal Erythroid Progenitors", *Biochem. Biophys. Res. Comm.* 148:694–700 (1987).

Perrine, S.P., et al., "Delay In The Fetal Globin Switch In Infants Of Diabetic Mothers", *N.E. J. Med.* 312:334–338 (1985).

Perrine, S., et al., "A Short–Term Trial Of Butyrate To Stimulate Fetal–Globin–Gene Expression In The β–Globin Disorders", *N.E. J. Med.* 328:81–86 (1993).

Perrine, S.P., et al., "Sodium Butyrate Enhances Fetal Globin Gene Expression in Erythroid Progenitors of Patients With Hb SS and β Thalassemia", *Blood* 74:454–459 (1989).

Platt, O., et al., "Pain In Sickle Cell Disease", *N.E. J. Med.* 325:11–16 (1991).

Poillon, W.N., et al., "Sparing effect of hemoglobin F and hemoglobin $A_2$ on the polymerization of hemoglobin S at physiologic ligand saturations", *Proc. Natl. Acad. Sci. USA* 90:5039–5043 (1993).

Simon, M.C., et al., "Rescue of erythroid development in gene targeted $GATA-1^-$ mouse embryonic stem cells", *Nature Genetics* 1(2):92–98 (1992).

Zhang, J–W., et al., "Butyrate Induces Expression of Transfected Human Fetal and Endogenous Mouse Embryonic Globin Genes in GM 979 Erythroleukemia Cells", *Devel. Gen.* 11:168–174 (1990).

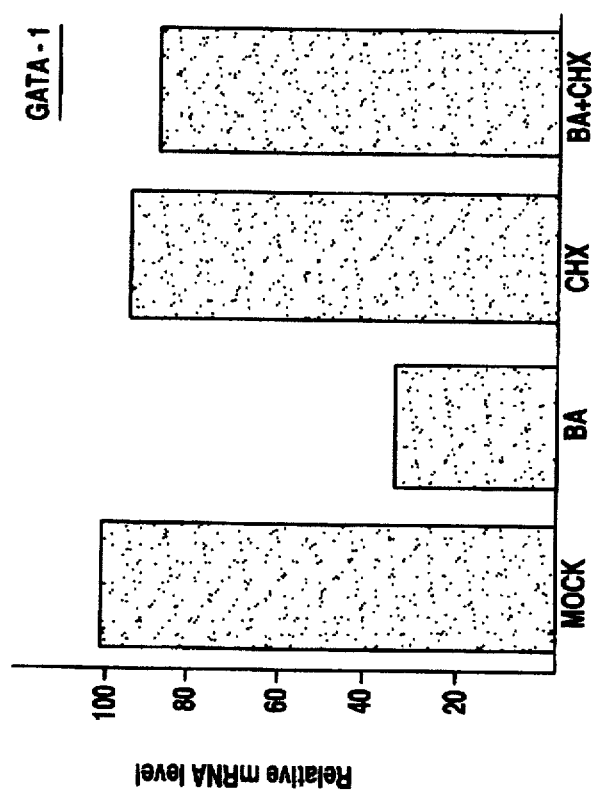
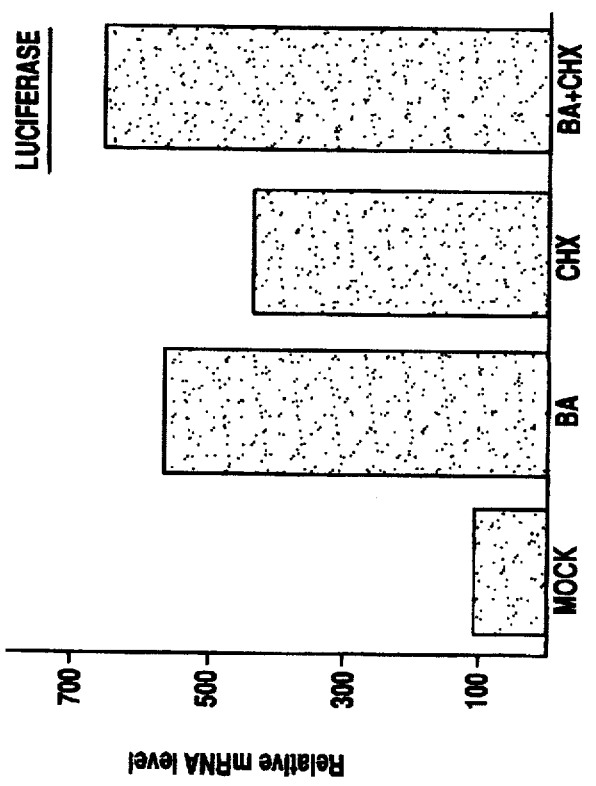
FIG.12A
FIG.12B (+) Indolactam V (−) Indolactam V

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:1:

GAATTCCAGA GCTTCTGGCA TTATAATCTA GC              32

( 2 ) INFORMATION FOR SEQ ID NO:2:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:2:

TTGATAACCT CAGACGTTCC AGAAGCGAGT G              31

( 2 ) INFORMATION FOR SEQ ID NO:3:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: oligonucleotide ( x i ) SEQUENCE DESCRIPTION: SEQ ID NO:3:

TTCACTCGCC GTTACTGAGG GAATCCTGGT TAG    33

( 2 ) INFORMATION FOR SEQ ID NO:4:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:4:

ACCAAAAAAC CTCGAGAAAT ACTTCCTA    28

( 2 ) INFORMATION FOR SEQ ID NO:5:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:5:

TAGTGTCTCG AGTATTAGTC AATAAAAA    28

( 2 ) INFORMATION FOR SEQ ID NO:6:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:6:

GAAGTGAACC TCGAGTTTAT ACAAGATA    28

( 2 ) INFORMATION FOR SEQ ID NO:7:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:7:

GCACACACAC TTCTCGAGTG GTAAATA    27

( 2 ) INFORMATION FOR SEQ ID NO:8:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:8:

CGGATAAGTA GATCTCGAGG TAAGCAT 27

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:9:

CACTGCACTC TCGAGAAATT AAGAGAT 27

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:10:

TTCACAATCC CTCGAGTTTT CAAAAAT 27

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:11:

CTCTATGCTC GAGGAAGGAA ACTAGCTAAA 30

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:12:

CCCCACCATA TCTCGAGGCA AATATCT 27

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:13:

```
GCCTTGCCTT AACCTCGAGC CTTGACAA                                                28
```

(2) INFORMATION FOR SEQ ID NO:14:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: oligonucleotide (xi) SEQUENCE DESCRIPTION: SEQ ID NO:14:

```
GGACTAGAAG CTTATTGATA ACCTCA                                                  26
```

INDUCERS OF GAMMA GLOBIN GENE EXPRESSION AND SCREENING ASSAYS THEREFOR

BACKGROUND OF THE INVENTION

Human β-like globin genes are encoded in a cluster located on chromosome 11. This cluster includes two genes encoding gamma, or fetal, globin ($\gamma^G$ and $\gamma^A$) and one gene encoding beta, or adult globin. Expression of globin genes is tightly regulated during ontogeny. A developmental switch from production of predominantly fetal hemoglobin (HbF; $\alpha_2\gamma_2$) to production of adult hemoglobin (HbA; $\alpha_2\gamma_2$) occurs beginning at about 28 to 34 weeks of gestation and continuing shortly after birth until HbA becomes predominant. This switch results primarily from decreased transcription of the gamma globin genes and increased transcription of the beta globin gene. The basis for many congenital hematological diseases is a defect in the structure or production of beta globin. For example, sickle cell anemia results from a point mutation in the beta globin structural gene, leading to production of abnormal HbS. β-thalassemias result from a partial or complete defect in the expression of the beta globin gene, leading to deficient or absent HbA.

Certain populations of adult patients with beta chain abnormalities have higher than normal levels of HbF and have been observed to have a milder clinical course of disease than patients with normal adult levels of HbF. For example, a group of Saudi Arabian sickle cell anemia patients who express 20–30% HbF have only mild clinical manifestations of the disease (Pembrey, M. E. et al. (1978) *Br. J. Haematol.* 40:415; Miller, B. A. et al. (1986) *Blood* 67:1404. There are also a variety of distinct genetic mutations which cause hereditary persistence of fetal hemoglobin, in which gamma globin gene expression is not downregulated during development. This condition has been shown to significantly decrease the severity of sickle cell anemia or β-thalassemia in individuals simultaneously afflicted with both traits (see e.g., Wood, W. G. and Weatherall, D. J. (1983) *Biochem. J.* 215:1–10). Genetic mutations leading to persistence of gamma globin gene expression have been assigned to at least three distinct loci, making it very unlikely that the ameliorating effect observed in individuals afflicted with both traits is due to a genetically linked trait unrelated to, but co-segregating with, hereditary persistence of fetal hemoglobin.

The beneficial effect of gamma globin gene expression as compensation for a defect in beta globin expression or structure has also been studied biochemically. Gamma globin has been shown to function as a chain terminator of the polymerization of deoxygenated Hb S that causes the pathology of sickle cell anemia (Poillon, W. N. et al. (1993) *Proc. Natl. Acad. Sci. USA* 90:5039–5043). Moreover, the maturation of malarial parasites is inhibited in erythrocytes that express fetal hemoglobin (Pasvol, G. et al. (1976) *Lancet* 1(7972):1269–1272; Luzzatto, L. et al. (1976) *Lancet* 1(7984):523–524; Cao, A. et al. (1977) *Lancet* 1(8004):202). Thus, there is both genetic and biochemical evidence that gamma globin gene expression can be therapeutically beneficial in a variety of clinical disorders.

While the developmental switch from gamma to beta globin gene expression is strictly controlled, there is evidence that external factors can influence gamma globin gene expression. For example, a delay in the fetal to adult hemoglobin switch has been observed in infants of diabetic mothers (Perrine, S. P. et al. (1985) *N. Eng. J. Med.* 312:334–338), suggesting an affect by circulating physiological factors. This phenomenon was traced to elevated plasma concentrations of α-amino-n-butyric acid in the diabetic mothers. Additional studies have demonstrated that butyric acid and certain derivatives thereof can delay the fetal to adult hemoglobin switch in vivo and increase gamma globin gene expression in vitro and in vivo (Perrine, S. P. et al. (1987) *Biochem. Biophys. Res. Comm.* 148:694–700; Perrine, S. P. et al. (1988) *Proc. Natl. Acad. Sci. USA* 85:8540–8542; Perrine, S. P. et al. (1989) *Blood* 74:454–459; Perrine, S. P. et al. (1993) *N. Eng. J. Med.* 328:81–86; Fibach, et al. (1993) *Blood* 82:2203–2209; U.S. Pat. No. 4,822,821; U.S. Pat. No. 5,025,029; PCT Publication No. WO 93/18761).

Additionally, butyric acid has been shown to induce differentiation of neoplastic and non-neoplastic cells (for a review see Newmark, H. L. et al. (1994) *Cancer Letters* 78:1–5). A study has demonstrated that butyric acid is a potent inducer of erythroid differentiation of cultured cells (Leder, A and Leder, P. (1975) *Cell* 5:319–322). In this study, a variety of butyric acid analogues and metabolites were also examined. The structural features of butyric acid were found to be quite stringently required for erythroid differentiating ability. For example, fatty acid chains longer than the 4-carbon butyric acid were ineffective at inducing erythroid differentiation.

The therapeutic use of butyric acid as an inducer of gamma globin gene expression and of cellular differentiation may have limitations. For example, very high dosages are necessary, requiring catheterization for continuous infusion of the compound, which is likely to reduce patient compliance. Moreover, high dosages of butyric acid can be associated with toxicity, in particular neurologic toxicity (Blau, A. C. et al. (1993) *Blood* 81:529–537). Accordingly, additional compounds capable of stimulating the expression of gamma globin, and methods for identifying such compounds, are still needed.

SUMMARY OF THE INVENTION

One aspect of the invention pertains to compounds useful for stimulating gamma globin gene expression and/or cellular differentiation. Preferred compounds of the invention include valeric (or pentanoic) acid and certain isomers, derivatives and homologues thereof, including, isovaleric (or isopentanoic) acid, methylthioacetic acid, and 4-pentynoic acid, and physiologically acceptable salts thereof. The compounds of the invention stimulate gamma globin gene expression with different kinetics than butyric acid, resulting in a more sustained induction of gamma globin gene expression. Moreover, the compounds of the invention are not toxic to cells at dosages at which butyric acid exhibits significant cellular toxicity.

In another embodiment, the invention pertains to use of an inhibitor of a short chain fatty acyl CoA dehyrogenase (SCAD) to stimulate gamma globin gene expression in a mammalian cell (e.g., erythroid cell) or to stimulate differentiation of a mammalian cell (e.g., malignant cell). Preferred inhibitors of SCAD include thioether and alkynoic derivatives of short chain fatty acids, such as methylthioacetic acid or 4-pentynoic acid, and pharmaceutically acceptable salts thereof. Gamma globin gene expression in a cell or differentiation of a cell can be stimulated by contact with an inhibitor of a SCAD, either alone or in combination with a short chain fatty acid (SCFA).

In another embodiment, the invention pertains to use of an activator of protein kinase C to stimulate gamma globin gene expression or cellular differentiation. A preferred activator of protein kinase C is (−) indolactam V. Gamma globin gene expression in a cell or differentiation of a cell can be stimulated by contact with an activator of protein kinase C, either alone or in combination with a SCFA.

The active compounds of the invention can be administered to a mammal to ameliorate β-globin disorders, such as sickle cell anemia and β-thalassemia. The compounds of the invention can also be administered to a mammal to prevent or ameliorate malaria. Furthermore, the compounds of the invention can be administered to a mammal to stimulate differentiation of cells, such as malignant cells (e.g., an erythroleukemia cell).

The invention further provides methods for identifying agents that stimulate gamma globin gene expression in mammalian cells. In one embodiment, agents that directly stimulate gamma globin gene expression are identified using a mammalian cell into which a nucleic acid molecule comprising a regulatory region of a gamma globin gene operatively linked to a reporter gene has been introduced. To identify an inducer of gamma globin gene expression, this cell is first contacted with an agent to be tested. Next, the reporter gene activity in the cell is measured. An increase in reporter gene activity in the presence of the agent, relative to reporter gene activity in the absence of the agent, is indicative that the agent stimulates gamma globin gene expression. The method is also useful for identifying agents that stimulate differentiation of cells. Moreover, the method can be used to identify agents that enhance the stimulation of gamma globin gene expression by SCFAs by contacting the cell both with an agent to be tested and with a SCFA. An increase in reporter gene activity in the presence of both the agent and the SCFA, relative to reporter gene activity in the presence of only the SCFA, is indicative that the agent enhances the stimulation of gamma globin gene expression by the SCFA.

Preferably, the cell used to identify inducers of gamma globin gene expression is an erythroid cell, more preferably a human erythroleukemia cell line such as K562. The nucleic acid molecule introduced into the cell typically comprises a human gamma globin gene promoter operatively linked upstream of the reporter gene. Preferably, the promoter fragment encompasses at least nucleotide residues −140 to −108 of the human gamma globin gene promoter. The nucleic acid molecule can further comprise a human gamma globin gene 3' enhancer operatively linked downstream of the reporter gene. Examples of suitable reporter genes for use in the method include genes encoding luciferase, chloramphenicol acetyltransferase, alkaline phosphatase and β-galactosidase. The nucleic acid can be introduced into a host cell in culture for an in vitro assay system or used to create a transgenic animal carrying the nucleic acid in its genome for an in vivo assay system.

The invention also encompasses isolated nucleic acid molecules and mammalian host cells and animals useful in the screening method of the invention. Furthermore, agents that stimulate gamma globin gene expression or cellular differentiation identified according to the methods disclosed herein are within the scope of the invention.

In another embodiment, the invention provides a method for identifying agents that stimulate transport of a SCFA, or derivative or salt thereof, into a mammalian erythroid cell. The method involves first contacting a mammalian erythroid cell (e.g., a human erythroleukemia cell line such as K562) with a SCFA, or derivative or salt thereof, and an agent to be tested. The SCFA, or derivative or salt thereof, is labeled with a detectable substance, such as a radioactive isotope.

Next the detectable substance associated with the mammalian erythroid cell is detected as an indicator of uptake of the SCFA, or derivative or salt thereof, by the cell. An increase in the amount of detectable substance associated with the cell in the presence of the agent, relative to the amount of detectable substance associated with the cell in the absence of the agent, is indicative that the agent stimulates transport of a SCFA, or derivative or salt thereof, into the mammalian erythroid cell. Preferred SCFA, or derivatives thereof, for use in the method are butyric acid, isobutyramide, valeric acid, isovaleric acid, 4-pentynoic acid and methylthioacetic acid, or salts thereof.

Agents that stimulate transport of a short chain fatty acid, or derivative or salt thereof, into a mammalian erythroid cell identified according to the method disclosed herein are within the scope of the invention. Such agents can be used in conjunction with a short chain fatty acid, or derivative or salt thereof, to stimulate gamma globin gene expression in a mammal.

BRIEF DESCRIPTION OF THE DRAWINGS

FIGS. 12A–B are graphic representations of the relative levels of luciferase mRNA (Panel A) and GATA-1 mRNA (Panel B) in K562 cells stably transfected with the gamma3'PE reporter gene construct upon treatment with butyric acid (BA) alone, cycloheximide (CHX) alone or butyric acid and cycloheximide (BA+CHX).

DETAILED DESCRIPTION OF THE INVENTION

Figure 1:
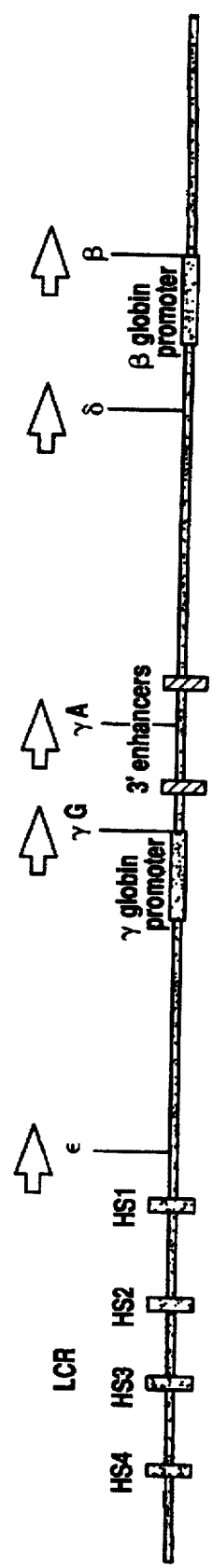
FIG. 1 is a schematic representation of the human globin gene locus depicting the relative positions of the different globin structural genes and cis-active regulatory elements.

This invention pertains to methods for stimulating gamma globin gene expression in a mammalian cell and methods for stimulating differentiation of a mammalian cell. The invention further pertains to compounds useful in the methods of the invention. The invention still further pertains to screening assays for identifying such compounds. Various aspects of the invention are described in further detail in the following subsections:

I. Compounds of the Invention and Compositions Thereof

One aspect of this invention pertains to compounds that can stimulate gamma globin gene expression in mammalian cells and/or stimulate differentiation of mammalian cells. In one embodiment, the compounds of the invention have the general formula I:

$$Z-W-\underset{\underset{R_1}{|}}{\overset{\overset{R_1}{|}}{C}}-R$$

wherein R is $CO_2R_2$, $SO_2R_2$, $SO_3R_2$, $CONR_3R_4$, $CONR_3OR_4$, $$\underset{C-O-C-R_2,}{\overset{O\;\;\;\;\;O}{\|\;\;\;\;\;\|}} \quad \underset{N^{\nearrow N},}{\overset{N\diagdown_N}{\underset{\diagup}{\langle\;\;\;|}}} \text{ or } \underset{C-O(CH_2)_n-}{\overset{O}{\|}}\!\!\!\!\!\!\!\!\!\!\!\!\!\bigcirc\!\!\!-R_5$$

and $R_2$ is H, M, $NH_2$, $C_{1-4}$ branched or linear alkyl or a partially or perfluorinated derivative thereof, and M is a cation; $R_3$ is H, $C_{1-3}$ alkyl or $C_{1-3}$ acyl; $R_4$ is H or $C_{1-3}$ alkyl; and $R_5$ is a halogen, $C_{1-4}$ alkoxy, $C_{1-4}$ alkyl, $NR_3R_4$ or $NO_2$;

$R_1$ is H or F;

W is S or $$\underset{Y}{\overset{R_1}{\underset{|}{\overset{|}{\underset{C}{\overset{|}{\phantom{C}}}}}}}$$

and Y is $R_1$, $CX_3$, $NH_2$ or $NH_3$, and X is H, F, Cl, Br or I, or combinations thereof;

and Z is a $C_{1-2}$ alkyl, alkenyl or alkynyl, or a partially or perfluorinated derivative thereof;

with the proviso that if W is $$\underset{R_1}{\overset{R_1}{\underset{|}{\overset{|}{\underset{C,}{\overset{|}{\phantom{C}}}}}}}$$

Z is a $C_2$ alkyl, alkenyl or alkynyl, or a partially or perfluorinated derivative thereof. Preferred cations (M) are alkali metals, e.g., sodium, potassium and the like.

Preferred compounds of the invention include valeric acid, isovaleric acid, 4-pentynoic acid and methylthioacetic acid, or pharmaceutically acceptable salts thereof. The term "pharmaceutically acceptable salt" refers to a salt that is physiologically compatible (i.e., non-toxic), such as a sodium salt or potassium salt.

As demonstrated in Example 3, stimulation of gamma globin gene expression in cells by treatment the active compounds of the invention results in higher levels of induction and/or more prolonged gamma globin gene expression than in cells stimulated by the same concentration of butyric acid (BA). Moreover, as demonstrated in Example 5, the active compounds of the invention exhibit significantly less cellular toxicity as dosages at which butyric acid is markedly cytotoxic. Additionally, the differential induction of mRNA encoding an erythroid specific transcription factor (GATA-1) by VA and IVA as compared to BA (see Example 4) suggest that VA and IVA stimulate gamma globin gene expression by a different mechanism than BA.

In another embodiment, the compound that stimulates gamma globin gene expression and/or cellular differentiation is an inhibitor of a short chain fatty acyl CoA dehydrogenase (SCAD). The term "short chain fatty acyl CoA dehyrogenase", as used herein, refers to a metabolic enzyme that catalyzes the degradation of short chain fatty acids. The term "short chain fatty acid", as used herein, refers to linear chain fatty acids having two to six carbons, and branched chain derivatives thereof. A preferred inhibitor of a SCAD is a thioether derivative of a short chain fatty acid, such as methylthioacetic acid, or a pharmaceutically acceptable salt thereof. Another preferred inhibitor of a SCAD is an alkynoic derivative of a short chain fatty acid, such as 4-pentynoic acid, or a pharmaceutically acceptable salt thereof.

Figure 13B:
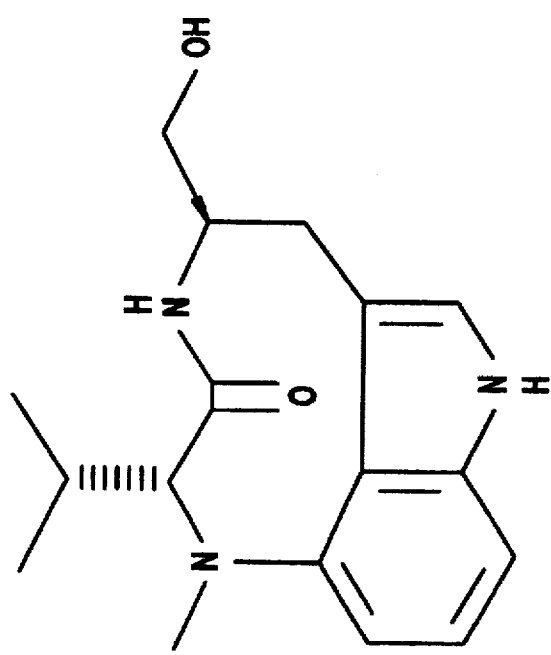
FIG. 13B is a schematic representation of the chemical structure of the inactive (+) stereoisomer of indolactam V.
Figure 13A:
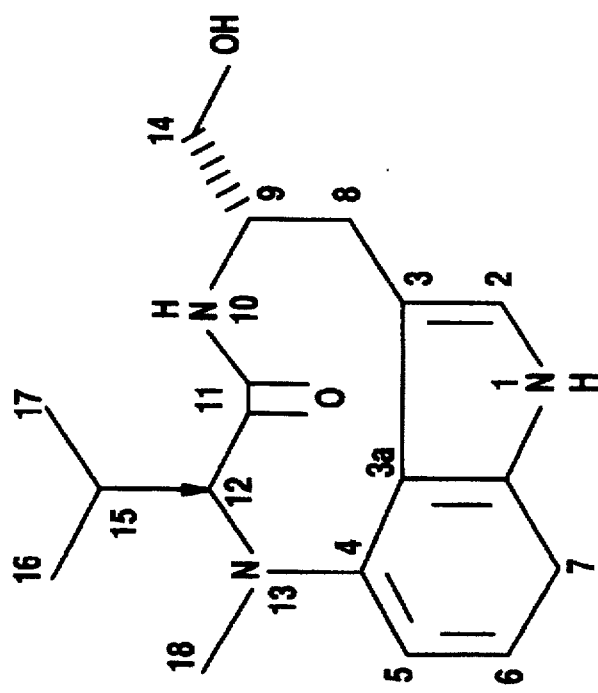
FIG. 13A is a schematic representation of the chemical structure of the active (−) stereoisomer of indolactam V.

In another embodiment, the compound that stimulates gamma globin gene expression and/or cellular differentiation is an activator of protein kinase C. A preferred activator of protein kinase C is the active (−) stereoisomer of indolactam V. The structures of (−) and (+) indolactam V are shown in FIG. 13A–B. As demonstrated in Example 7, short chain fatty acid-mediated induction of gamma globin gene expression involves a signal transduction pathway that intersects with activated protein kinase C. The protein kinase C activator (−) indolactam V is capable of stimulating gamma globin gene expression on its own and, moreover, enhances the stimulation of gamma globin gene expression by a short chain fatty acid (e.g., butyric acid) when used in combination with the short chain fatty acid.

The compounds of the invention are commercially available (e.g., from Aldrich Chemical Co., Milwaukee, Wis. or Sigma Chemical Co., St. Louis, Mo.) or can be synthesized by standard techniques known in the art. The compounds of the invention further can be incorporated into compositions suitable for pharmaceutical administration. The compositions typically include a compound of the invention and a pharmaceutically acceptable carrier, and optionally other therapeutic agents. The term "pharmaceutically acceptable carrier" refers to a carrier that is physiologically compatible with an intended recipient and compatible with other ingredients in the formulation. Examples of acceptable carriers include physiologically compatible solvents, solutions and dispersion media, for example, water, isotonic saline, ethanol, polyol (for example, glycerol, propylene glycol, and liquid polyethylene glycol, and the like), and suitable mixtures thereof. Buffers, antioxidants, antimicrobial agents and the like may also be included in the formulation. Additional therapeutic agents that can be included in the composition include other agents that stimulate gamma globin gene expression, delay the gamma to beta globin switch and/or stimulate erythroid differentiation. Examples of other agents that can be included in the composition include another of the active compounds disclosed herein, butyric acid, isobutyramide, erythropoietin, inhibin, activin, hydroxyurea and 5-azacytidine.

The pharmaceutical composition may vary depending upon the intended route of administration of the compound. Pharmaceutical compositions suitable for injectable use include sterile aqueous solutions (where water soluble) or dispersions, and sterile powders for the extemporaneous preparation of injectable solutions or dispersion. Sterile injectable solutions can be prepared by incorporating the active compound in the required amount in an appropriate solvent, followed by filter sterilization. Generally, dispersions are prepared by incorporating the active compound into a sterile vehicle which contains a basic dispersion medium and any other ingredients. In the case of sterile powders for the preparation of sterile injectable solutions, the preferred methods of preparation are vacuum drying and freeze-drying from a previously sterile-filtered solution, which yields a powder of the active compound plus any additional desired ingredients. The solution, dispersion or powder must be stable under the conditions of manufacture and storage and may be preserved against the contaminating action of microorganisms by various antibacterial and antifungal agents, for example, parabens, chlorobutanol, phenol, ascorbic acid, thimerosal, and the like. The proper fluidity of injectable solutions can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Compositions suitable for oral administration can also be prepared. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent.

The active compounds of the invention can also be incorporated into a time release formulation, for example in a composition which includes a slow release polymer. The active compound can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

It is especially advantageous to formulate compositions in dosage unit form for ease of administration and uniformity of dosage. Dosage unit form refers to physically discrete units suited as unitary dosages, e.g., daily dosages, for the mammalian subjects to be treated; each unit containing a predetermined quantity of active compound calculated to produce the desired therapeutic effect in association with the required pharmaceutical carrier. A compound of the invention is included in a pharmaceutical composition in a therapeutically effective amount sufficient to induce gamma globin gene expression in a mammal. The therapeutically effective amount may vary depending upon the weight and tolerance of the subject to be treated, the severity of the disorder to be treated, the desired therapeutic result, and the particular active compound(s) used.

II. Uses of the Compounds of the Invention

The compounds of the invention are useful for stimulating gamma globin gene expression in mammalian erythroid cells. The ability of the compounds of the invention to stimulate gamma globin gene expression can be used therapeutically in the treatment of β-globin disorders. The term "β-globin disorder" refers to diseases characterized by a defect in the structure or production of β-globin, including sickle cell anemia and β-thalassemias. Additionally, in another embodiment, the ability of the compounds of the invention to stimulate gamma globin gene expression can be exploited therapeutically in the prevention or treatment of malaria. Furthermore, in yet another embodiment, the compounds of the invention can be used to stimulate differentiation of mammalian cells, such as malignant cells. The term "malignant cell", as used herein, refers to a neoplastic or transformed cell. Preferred malignant cells to be differentiated according to the methods of the invention include leukemias, such as erythroleukemias.

In one embodiment of the methods of the invention, a mammalian cell is contacted with a compound of the invention to stimulate gamma globin gene expression in the cell. In another embodiment, a mammalian cell is contacted with a compound of the invention to stimulate differentiation of the cell. The term "stimulating" is intended to encompass both inducing a particular result (e.g., gamma globin gene expression or differentiation) and enhancing the level or degree of a particular result. The term "contacting" is intended to include incubating or culturing cells in the presence of the compound and administering the compound to a mammal to thereby contact cells in vivo.

A cell (e.g., an erythroid cell) can be contacted with a compound of the invention in vitro for purposes of determining the efficacy of gamma globin gene induction or cellular differentiation by a particular active compound prior to a course of in vivo treatment. Alternatively, erythroid cells treated in vitro with an active compound of the invention can be reintroduced into a subject for therapeutic purposes. A non-limiting example of an effective treatment regimen for in vitro induction of gamma globin gene expression is incubation of the erythroid cells with the active compound at a concentration of 5 mM for 48 to 122 hours.

To stimulate gamma globin gene expression of differentiation in a mammalian subject in vivo, a compound of the invention is administered to the mammal. The route of administration should be chosen to result in an increased plasma concentration of the active compound. Preferably the compound is administered intravenously, although insofar as other routes of administration lead to increased plasma concentrations of the compound, these routes of administration (e.g., oral, parenteral) are also contemplated. In one embodiment, the compound, preferably in a sterile injectable pharmaceutical composition, is introduced into the bloodstream of the mammalian subject by continuous intravenous infusion. The compound can also be injected, or otherwise administered, as a single bolus or in divided dosages over a period of time.

The frequency of administration and dosage of the active compound will depend upon the particular compound used, the age, size and weight of the subject being treated, the condition of the subject, etc. In one embodiment, the active compound is administered to a mammalian subject (e.g., human, monkey, horse, dog, cat, etc.) suffering from, or susceptible to, a β-globin disorder. In another embodiment, the active compound is administered to a subject suffering from or susceptible to malaria. In yet another embodiment, the active compound is administered to a subject with a malignancy (e.g., a leukemia or minor). Due to the variables affecting the therapeutic dosage described above, a "therapeutically effective" amount of active compound is determined at the discretion of the attendant physician. Non-limiting examples of effective dosage ranges are 1 mg to 10 gm/kg/day, more preferably 10 mg to 1 gm/kg/day, even more preferably 100 mg to 1 gm/kg/day. The plasma concentration of active compound can be monitored by standard techniques, e.g., gas chromatography. The proportion of reticulocytes in a treated subject producing hemoglobin F can be assessed by known methods, such as those described in Papayannopoulou, T. et al. (1980) *Br. J. Haematol.* 44:535; Boyer, S. H. et at. (1984) *Blood* 64:1053–1058; Charache, S. et al. (1987) *Blood* 69:109–116.

In one embodiment, the active compound used to stimulate gamma globin gene expression or cellular differentiation is an inhibitor of a short chain fatty acyl CoA dehyrogenase, such as methylthioacetic acid or 4-pentynoic acid. While not intending to be limited by mechanism, such an inhibitor, by inhibiting an enzyme responsible for degradation of short chain fatty acids, it thought to stimulate gamma globin gene expression or cellular differentiation by increasing the concentration of endogenously produced short chain fatty acids. Stimulation of gamma globin gene expression or cellular differentiation may be further promoted by coadministering the SCAD inhibitor and a short chain fatty acid(s), or derivative or salt thereof, e.g., butyric acid, isobutyramide, valeric acid or isovaleric acid.

In another embodiment, the active compound used to stimulate gamma globin gene expression or cellular differentiation is an activator of protein kinase C, e.g., (−) indolactam V. Such an activator can be administered to a subject on its own, or alternatively may be coadministered with a short chain fatty acid, e.g., butyric acid, isobutyramide, valeric acid or isovaleric acid. As demonstrated in Example 6, (−) indolactam V synergizes with butyric acid to stimulate gamma globin gene expression.

III. Screening Assays of the Invention

Another aspect of the invention pertains to methods for identifying agents that stimulate gamma globin gene expression, either by directly stimulating gene expression in an erythroid cell or by stimulating transport into an erythroid cell of a short chain fatty acid, or derivative thereof, that itself stimulates gamma globin gene expression.

In one embodiment, the screening method of the invention involves contacting a mammalian cell with an agent to be tested, wherein a nucleic acid molecule comprising a regulatory region of a gamma globin gene operatively linked to a reporter gene has been introduced into the mammalian cell. The reporter gene activity in the mammalian cell is then measured as an indicator of gamma globin gene expression. An increase in reporter gene activity in the presence of the agent, relative to reporter gene activity in the absence of the agent, is indicative that the agent stimulates gamma globin gene expression.

The nucleic acid molecule introduced into the cell (also referred to herein as the reporter construct) includes a human gamma globin gene regulatory region operatively linked to the reporter gene. Suitable gamma globin regulatory regions include promoter and enhancer fragments. The regulatory region is "operatively linked" to the reporter gene in such a manner as to allow for transcription of the reporter gene under the control of the regulatory region (e.g., a promoter fragment is linked upstream of the reporter gene by phosphodiester bonds in a 5' to 3' direction within a distance that allows for appropriate regulatory control of the reporter gene). A DNA fragment encompassing ≈1200 nucleotides of the human gamma globin gene promoter can be obtained by the polymerase chain reaction using oligonucleotide primers described in Example 1, or smaller fragments thereof can be obtained using oligonucleotide primers described in Example 7. A preferred promoter fragment encompasses at least nucleotides −140 to −108 (relative to the start site of transcription). A human gamma globin promoter fragment can be cloned upstream (i.e., 5') of a reporter gene by standard recombinant DNA techniques using commercially available reporter gene plasmids (e.g., the pGL2 luciferase plasmid from Promega). In addition to a human gamma globin gene promoter fragment, the reporter construct preferably also includes a human gamma globin 3' enhancer fragment. A DNA fragment encompassing the 3' proximal enhancer of the human gamma globin gene (as described in Bodine, D. and Ley, T. J. (1987) *EMBO J.* 6:2997–3004) can be obtained by the polymerase chain reaction using oligonucleotide primers described in Example 1. This fragment can be cloned downstream (i.e., 3') of a reporter gene by standard recombinant DNA techniques.

In addition to gamma globin regulatory elements, the reporter construct also includes a reporter gene. Reporter genes are well known in the art and preferably encode a gene product that is readily assayable, e.g., an enzyme whose activity is readily detectable. A preferred reporter gene encodes luciferase. Other suitable reporter genes encode chloramphenicol acetyltransferase gene, an alkaline phosphatase gene and a beta-galactosidase gene.

The reporter gene construct can be introduced into a mammalian cell by a suitable technique for introducing nucleic acid into eukaryotic cells. Examples of art-recognized techniques for introducing nucleic acid into mammalian cells include electroporation, calcium phosphate coprecipitation, DEAE-dextran transfection, lipofection and the like. The reporter gene construct can be introduced into cells transiently, or stably transfected cells can be selected. To select stable transfectants, a gene encoding a selectable marker (e.g., drug resistance) is typically cotransfected with the reporter gene construct.

The reporter gene construct is preferably introduced into a mammalian erythroid cell, more preferably a human erythroid cell. A preferred cell line for use in the screening assay is the human erythroleukemia cell line K562 (ATCC No. CCL 243, Rockville, Md.). Non-limiting examples of other suitable host cells are MEL, Radscher, HEL, KB and GM979.

In addition to host cells in culture, the reporter gene constructs of the invention can be used to create a transgenic animal (e.g., mouse) that carries the reporter gene construct in their genome. The reporter gene construct can be introduced into a fertilized oocyte by standard techniques and the oocyte implanted into a foster mother. The offspring are then screened for the presence of the transgene (i.e., reporter gene construct) in their genome. Accordingly, the term mammalian host cell is intended to encompass both cells in culture and cells within a host animal.

To identify a compound that stimulates gamma globin gene expression, a mammalian cell carrying a reporter gene construct of the invention is contacted with a test compound and the reporter gene activity in the cell is measured. For example, host cells in culture can be incubated with the test compound or the test compound can be administered to a host animal (i.e., transgenic animal). Measurement of "reporter gene activity" typically involves assaying the enzymatic activity of the gene product encoded by the reporter gene (e.g., measuring luciferase activity by a standard luciferase assay), but can also be accomplished by measuring the amount of reporter gene mRNA present in the cell (e.g., by Northern hybridizations, RNase protection assays or revere transcriptase-PCR) or by immunological detection of the gene product encoded by the reporter gene (e.g., by immunohistochemistry or enzyme linked immunosorbent assay). The amount of reporter gene activity in a cell treated with a test compound is compared to a control amount present in untreated cells. Agents that stimulate gamma globin gene expression are identified based upon their ability to increase the amount of reporter gene activity in treated cells.

The screening assay of the invention utilizing a gamma globin gene reporter construct, described above, is also useful for identifying agents that stimulate differentiation of a mammalian cell. In this embodiment, the ability of an agent to stimulate reporter gene activity in the host cell is used as an indicator of cellular differentiation.

In another embodiment, the reporter gene assay described herein is used to identify an agent that enhances gamma globin gene expression by a short chain fatty acid. To identify an agent that enhances (i.e., increases or synergizes with) the gamma globin stimulating-activity of a SCFA, a mammalian cell carrying a gamma globin reporter gene construct is contacted with an agent to be tested together with a SCFA (e.g., butyric acid) and the reporter gene activity in the cell is measured. An increase in reporter gene activity in the presence of both the agent and the SCFA, relative to reporter gene activity in the presence of only the SCFA, is indicative that the agent enhances the stimulation of gamma globin gene expression by the SCFA.

Additional assays can be carried out to determine whether an active compound identified by the reporter gene assay described herein stimulates gamma globin gene expression in a specific manner. For example, cells can be treated with the active compound and the cellular proteins induced by the treatment can labeled by standard techniques (e.g., by culturing the cells in the presence of $^{35}$S-methionine during treatment with the agent). Total cellular proteins can then be analyzed (e.g., by SDS-PAGE) to identify newly synthesized proteins induced by treatment with the active compound. Additionally or alternatively, mRNAs induced by treatment with the active compound can be analyzed by standard techniques, such as differential display PCR (Liang, P. and Pardee, A. B. (1992) *Science* 257:967–971).

Additional assays can also be carried out to determine whether an active compound identified by the reporter gene assay described herein directly stimulates gamma globin gene expression or indirectly stimulates gamma globin gene expression by inhibiting the activity of short chain fatty acyl CoA dehydrogenase (SCAD). The ability of a test compound to inhibit SCAD activity can be assessed by treating cells with the compound and measuring the endogenous levels of short chain fatty acids, such as butyric, valeric or isovaleric acid. Endogenous short chain fatty acid concentrations will be increased in the presence of an inhibitor of SCAD. The increased amounts of endogenous short chain fatty acid (e.g., butyric acid) may then lead to direct stimulation of gamma globin gene expression by the SCFAs.

As demonstrated in Example 6, stimulation of gamma globin gene expression by a short chain fatty acid (e.g., butyric acid) involves transport of the SCFA that requires a potassium gradient. Accordingly, in another embodiment, the invention provides a method for identifying an agent that stimulates transport of a short chain fatty acid, or derivative or salt thereof, into a mammalian erythroid cell. The method involves first contacting a mammalian erythroid cell with a short chain fatty acid (SCFA), or derivative or salt thereof, and an agent to be tested. The short chain fatty acid, or derivative or salt thereof, is labeled with a detectable substance, such as a radioactive isotope or fluorescent marker. The detectable substance associated with the mammalian erythroid cell is then detected as an indicator of uptake of the SCFA, or derivative or salt thereof, by the cell. For example, association of a radiolabeled SCFA with the cell can be detected and quantitated by scintillation counting of the cells. An increase in the amount of detectable substance associated with the cell in the presence of the test agent, relative to the amount of detectable substance associated with the cell in the absence of the agent, is indicative that the agent stimulates transport of a short chain fatty acid, or derivative or salt thereof, into the mammalian erythroid cell. Preferred SCFA, or derivatives, for use in the screening method are butyric acid, valeric acid, isovaleric acid, 4-pentynoic acid, methylthioacetic acid, and derivatives and salts thereof. A preferred erythroid cell for use in the screening assay is a human erythroleukemia cell, such as a K562 cell.

An agent that stimulates transport of a short chain fatty acid, or derivative or salt thereof, into a mammalian erythroid cell identified according to the screening method of the invention can be used in conjunction with a SCFA, or derivative or salt thereof, to stimulate gamma globin gene expression in a mammal. The agent and the SCFA, or derivative or salt, can be coadministered to a mammal to ameliorate a β-globin disorder or malaria. The ability of the agent to increase transport of the SCFA, or derivative or salt, into erythroid cells may reduce the therapeutically effective dosage of SCFA and/or may increase the level of induction of gamma globin gene expression by the SCFA in the mammal.

This invention is further illustrated by the following examples which should not be construed as limiting. The contents of all references and published patents and patent applications cited throughout the application are hereby incorporated by reference.

EXAMPLE 1

Preparation of Gamma Globin-Reporter Gene Constructs

The entire human globin gene locus, spanning approximately 150 kilobases, is shown schematically in FIG. 1. Depicted are the different globin structural genes and cis-active regulatory elements (e.g., promoters and enhancers). To construct gamma globin reporter gene plasmids, nucleic acid fragments comprising nucleotide sequences normally flanking (i.e., at either the 5' or 3' end of) the gamma globin gene were obtained and subcloned into a plasmid encoding a reporter gene. The human gamma globin 5' promoter fragment consisted of nucleotides −1200 to +30, relative to the start site of transcription (nucleotide numbers 38205 to 39435 of the human gamma globin gene in the GENEMBL database, accession number J00179). The promoter fragment was obtained from human genomic DNA by polymerase chain reaction (PCR) amplification using oligonucleotide primers of the sequences:
(−1230/−1200) GAATTCCAGAGCTTCTGGCAT-TATAATCTAGC (SEQ ID NO: 1)
(+1/+30) TTGATAACCTCAGACGTTCCAGAAGC-GAGTG (SEQ ID NO: 2)
The identity of the amplified fragment was verified by DNA sequencing. The 3' enhancer fragment corresponds to the 3' enhancer fragment described in Bodine, D. and Ley, T. J. (1987) *EMBO J.* 6:2997–3004. This fragment encompasses nucleotides 41390 to 42140 of the human gamma globin gene in the GENEMBL database, accession number 100179.

Figure 2:
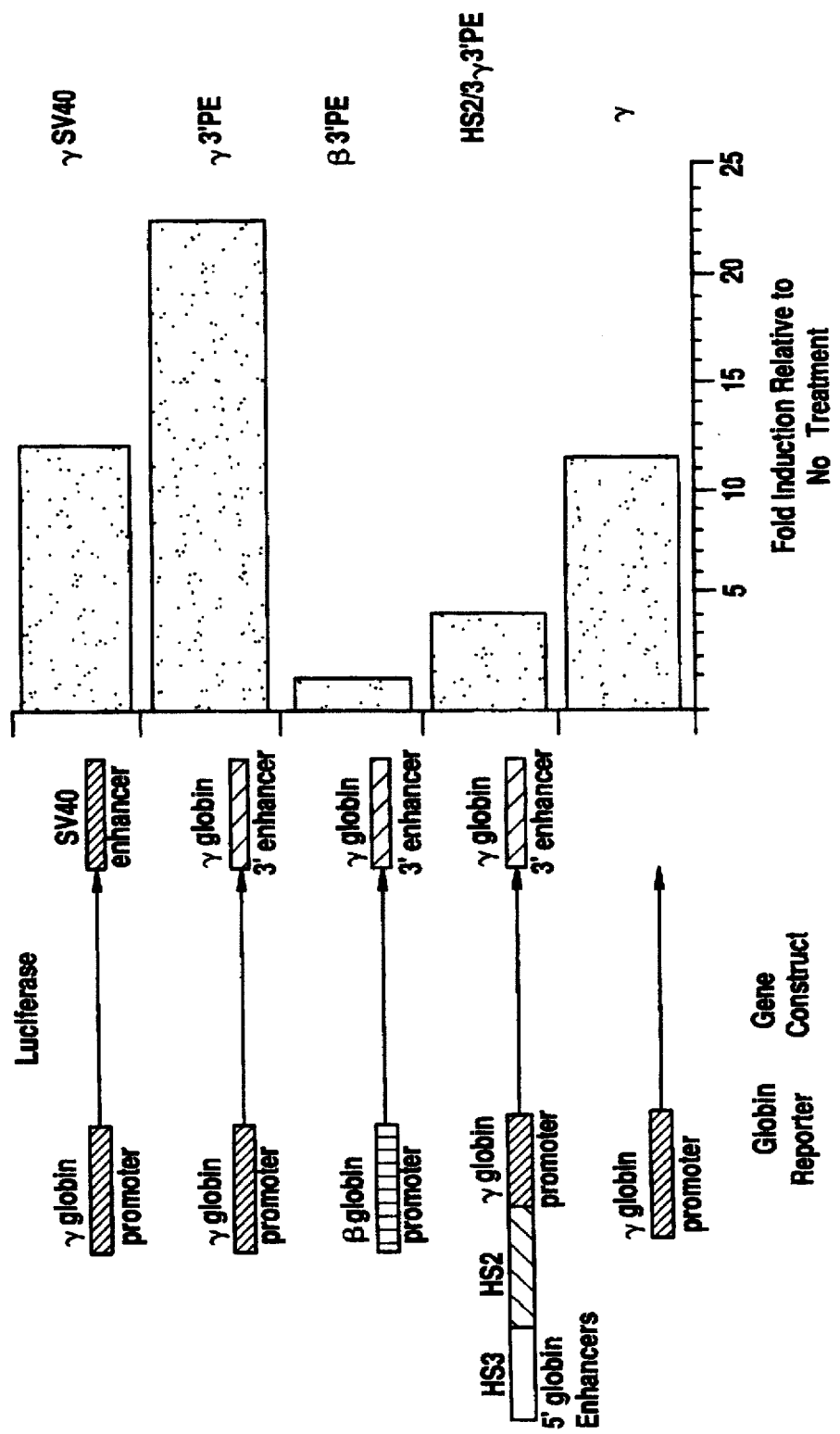
FIG. 2 is a graphic representation of butyric acid-induced expression of different gamma globin-reporter gene constructs transiently transfected into K562 cells.

The gamma globin 5' promoter and 3' enhancer fragments, alone or in combination with each other or another fragment, were inserted into restriction endonuclease sites flanking the coding sequences of the luciferase gene in pGL2 using standard recombinant DNA techniques (pGL2 was obtained commercially from Promega Biotech). Constructs were prepared which contained: 1) the gamma globin promoter alone upstream of the luciferase gene (gamma); 2) the gamma globin promoter upstream of the luciferase gene and the gamma globin 3' enhancer downstream of the luciferase gene (gamma3'PE); 3) the gamma globin promoter upstream of the luciferase gene and the SV40 enhancer downstream of the luciferase gene (gammaSV40); 4) the beta globin promoter upstream of the luciferase gene and the gamma globin 3' enhancer downstream of the luciferase gene Coeta3'PE); and 5) hypersensitive sites 2 and 3 G-IS2 and HS3) of the 5' globin enhancer upstream of the gamma globin promoter upstream of the luciferase gene and the gamma globin 3' enhancer downstream of the luciferase gene (HS2/3gamma3'PE). These constructs are illustrated schematically in FIG. 2.

EXAMPLE 2

Introduction of Gamma Globin-Reporter Gene Constructs into Host Cells

The gamma globin-luciferase reporter gene constructs described in Example 1 were introduced into a human erythroleukemia cell line K562 (ATCC No. CCL 243). To create stable transfectants, K562 cells ($5 \times 10^6$) in log phase were suspended in 400 µl HEPES buffered saline and then combined with 33.5 µg salmon testes DNA (Sigma), 1.5 µg neo plasmid (pPMT) and 15 µg reporter gene plasmid supercoiled that had been co-precipitated and suspended in 400 µl HEPES buffered saline. The DNA-cell mixture was electroporated at settings of 0.25 KV and 960 µFD using a Gene Pulser (BioRad Inc.) electropotation apparatus.

The cells were allowed to recover 10 minutes at room temperature, then added to 10 ml complete RPMI cell culture medium. Cell debris was removed by centrifugation at 1000 rpm for 5 minutes. The live cells were suspended in 20 ml RPMI in $2 \times 10$ cm dishes and grown in non-selective media for 48 hours. Stably transfected cells were then selected by growing the cells in media containing 300 µg/ml G418 for about one month. During this time the cells were split 1:5 every 3 to 4 days. Once the lines were stable, they were carried in 100 µg/ml G418. The cell lines were designated according to the reporter gene construct that was introduced into the cell line. For example, a cell line carrying the gamma'3PE construct was designated gamma3'PE. Transient transfections were carried out similarly except that the neo plasmid was omitted from the electroporation solution and the cells were not subjected to G418 selection.

EXAMPLE 3

Use of Gamma Globin-Reporter Gene Constructs to Identify Inducers of Globin Gene Expression K562 host cells carrying gamma globin-reporter gene constructs were used to lo screen compounds for their ability to induce globin gene expression, as measured by increased reporter gene activity in the host cells upon treatment with the compound. The host cells described in Example 2 were grown to log phase cells and plated at a density of $2 \times 10^5$/ml in RPMI media without G418. After 24 hours, compounds to be assayed for their ability to induce globin gene expression were dissolved in RPMI media at a concentration of 5 mM and added to the K562 stable transfectants. Mock-treated stably transfected K562 cells served as a negative control. The cells were incubated with the test compounds at 37° C. for various time periods (e.g., 24, 50, 74 and 122 hours).

After induction with the test compounds, the cells were harvested, lysed and assayed for reporter gene activity (i.e., luciferase activity) as follows. Cells were collected, washed once with PBS and lysed in 200 µl Cell Culture Lysis 1 X Reagent (Promega Luciferase Assay System) consisting of 25 mM Tris-Phosphate pH 7.8; 2 mM DTT; 2 mM 1,2-diaminocyclohexane-N,N,N,N-tetraacetic acid; 10% glycerol; 1% Triton X-100. Nuclei were pelleted at 14,000 rpm for 20 seconds in a microfuge and the supernatant was assayed for luciferase activity immediately or stored at −20° C. until thawed for assay.

To assay the cell supernatant for luciferase activity, 20 µl of each lysate was pipetted into a well of a Wallace 96 well sample plate. 100 µl Luciferase Assay Reagent (Promega), consisting of 20 mM Tricine; 1.07 mM $(MgCO_3)_4Mg(OH)_2 \times 5H_2O$; 2.67 mM $MgSO_4$; 0.1 mM EDTA; 33.3 mM DTT; 270 µM coenzyme A; 470 µM luciferin; 530 µM ATP; final pH 7.8, was added to each sample. The luminescence of the assay plate was immediately measured using a Microbe (Wallace Inc.) plate reader liquid scintillation counter.

To normalize luciferase units to the number of viable cells, parallel cell viability assays were performed using 3-(4,5-dimethylthiazol-2-yl)-2,5-diphenyltetrazolium bromide (MTT) (Vistica, D. T. et al. (1991) *Cancer Res.* 51:2515–2520). Transfected K562 cells were plated in 96 well dishes at a density of $2 \times 10^4$ and $2 \times 10^3$ cells per 100 µl per well. 24 hours later, the cells were treated with test compounds (at a final concentration of 5 mM). At 24, 50, 74 or 122 hours after treatment, 50 µl of 3 mg/ml MTT in PBS was added to each well. The 96 well plate was then incubated at 37° C. for 4 to 5 hours. The formazan derivatives formed from tetrazolium by viable cells were solubilized by the addition of 50 µl/well 25% SDS, pH 3, overnight at 37° C. The plates were than read at a wavelength of 550 nm.

Comparison of Inducibility of Different Reporter Gene Constructs

In a first series of experiments, K562 cells transiently transfected with the different gamma globin-reporter genes described in Example 1 were treated with butyric acid (BA). After treatment, the level of reporter gene activity (i.e., luciferase activity) in the treated cells was compared to determine the BA-inducibility of the different reporter gene constructs. The results are shown graphically in FIG. 2, which illustrates the fold induction of luciferase activity by BA relative to untreated cells. Among the cis-active sequence tested, the combination of the gamma globin promoter and the gamma globin 3' Proximal Enhancer flanking the luciferase gene (gamma3'PE) proved to be most responsive to BA. All other constructs tested (including gammaSV40, beta3'PE, HS2/3gamma3'PE and gamma) were at least 2 fold less responsive to BA treatment. Promoterless constructs containing only the luciferase gene or the luciferase gene fused to the 3'Proximal Enhancer were not induced by BA. Furthermore, a construct containing the beta globin promoter fused to the luciferase gene in the context of the 3'Proximal Enhancer (beta3'PE) was not inducible, indicating that the gamma globin promoter was essential for the response. Consistent with this, a construct containing the gamma globin promoter without the 3' Proximal Enhancer (gamma) was inducible, albeit to a lesser extent than when in the context of the 3' Proximal Enhancer (gamma3'PE).

To test whether the increased sensitivity of the gamma globin promoter to BA was due to a specific property of the globin 3' Proximal Enhancer or if this was a property of transcriptional enhancers in general, two copies of the 72 bp repeat of the SV40 enhancer (isolated by PCR from the simian virus 40 genome) were substituted for the 3' Proximal Enhancer in the context of the gamma globin promoter (construct gammaSV40). The results showed the SV40 sequence was not effective in augmenting the responsiveness of the gamma globin promoter to BA, indicating that the 3' Proximal Enhancer sequences uniquely function synergistically with the gamma globin promoter in mediating the response to BA. Surprisingly, sequences from the globin locus 5' enhancer (or locus control region, LCR) appear to reduce the sensitivity of the gamma3'PE construct to BA (compare the activity of HS2/3gamma3'PE to gamma3'PE). This may be due to the unnatural proximity of these enhancer sequences to the gamma globin promoter in this construct. Normally, these sequence reside over 30 kB upstream of the promoter and one function of BA in vivo may be to promote interaction between the chromosomal LCR sequences and the gamma globin promoter. Artificially positioning the LCR components near the gamma globin promoter may have in fact complemented the effect of BA. Thus, empirically, it appears that maintaining the cis-active elements of the gamma globin locus in their natural context is important for developing the most sensitive reporter gene assay system for detecting gone induction by short chain fatty acids such as BA.

Screening of Short Chain Fatty Acids for Induction of Reporter Gene Activity

Figure 3:
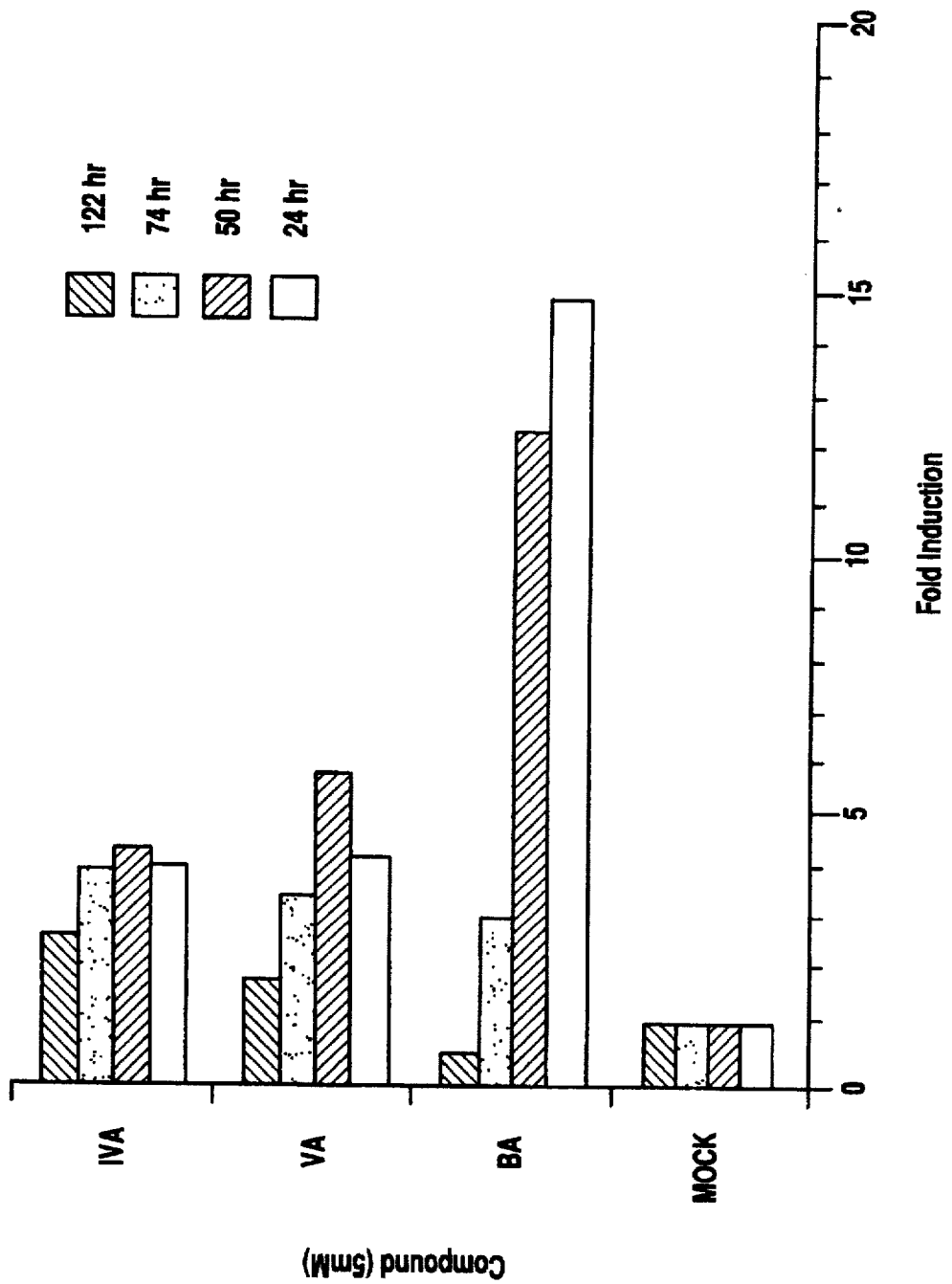
FIG. 3 is a graphic representation of reporter gene activity in K562 cells stably transfected with the gamma3'PE construct upon induction with butyric acid (BA), valeric acid (VA) or isovaleric acid (IVA). Luciferase units are normalized to the number of live cells.
Figure 4:
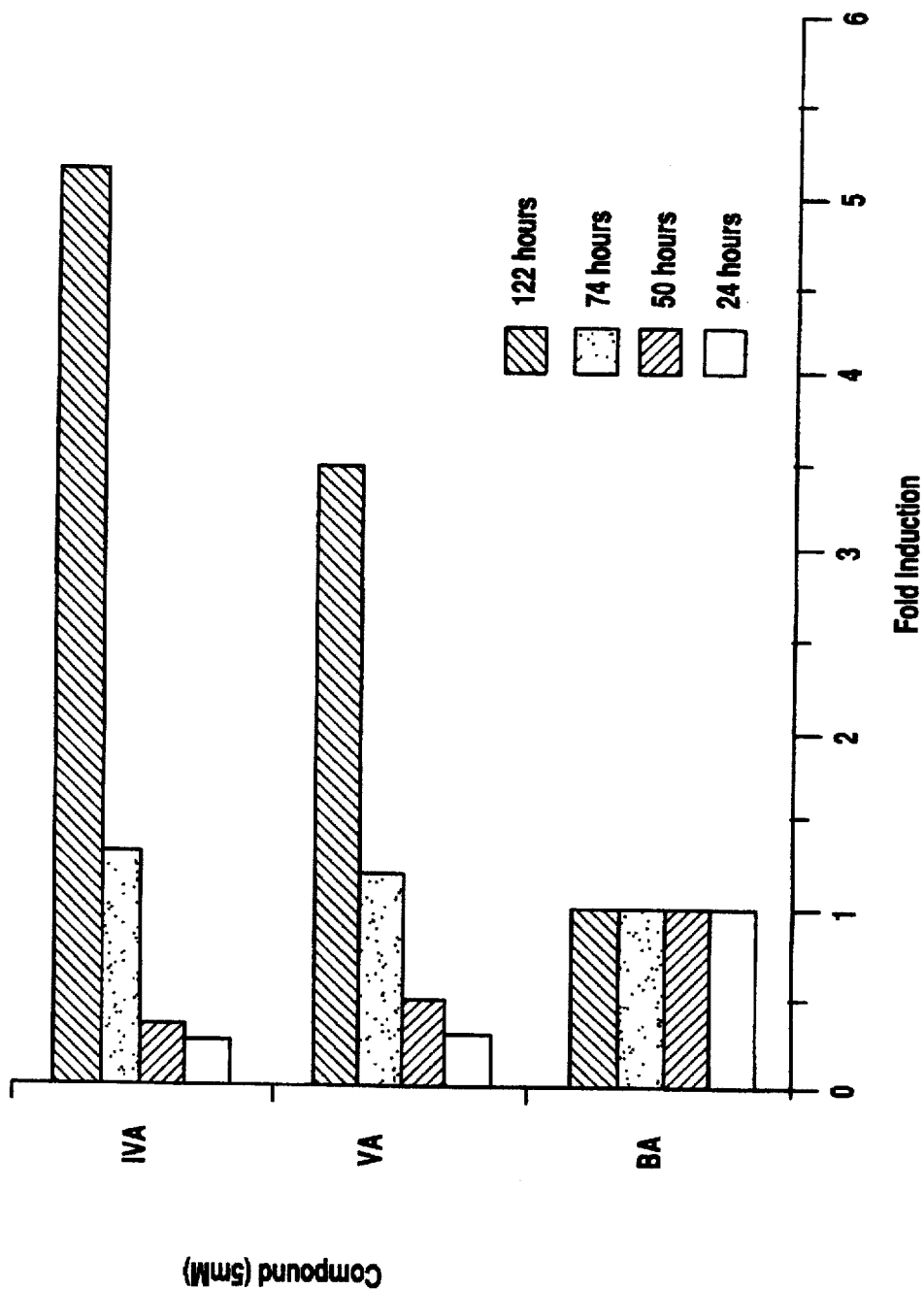
FIG. 4 is a graphic representation of reporter gene activity in K562 cells stably transfected with the gamma3'PE construct upon induction with butyric acid (BA), valeric acid (VA) or isovaleric acid (IVA). Luciferase units are normalized to reporter gene activity induced by BA treatment.

The comparison of the inducibility of the different gamma globin-reporter gene construct, described above, indicated that the gamma3'PE construct displayed the strongest inducibility upon BA treatment. Accordingly, a stable transfect of K562 carrying this construct (referred to as the gamma3'PE cell line) was used to screen other compounds for their ability to induce reporter gene activity. The gamma 3'PE cells were treated with different short chain fatty acids and the induced luciferase activity was assayed as described above. Initial experiments indicated that valeric acid (VA) and isovaleric acid (IVA) exhibited an ability to induce reporter gene expression. These compounds were thus studied further. To compare the ability of VA, IVA and BA to induce gamma-globin gene expression, gamma 3'PE cells were treated with each compound at a final concentration of 5 mM. Cells were harvested at time points ranging from 24–122 hr post induction. To control for potential toxic or cytostatic effects of BA non-specifically affecting the apparent level of gene induction, the results were normalized to the number of viable cells present in the cultures at the time of harvest as determined by MTT assays (as described above). As shown in the data illustrated graphically in FIG. 3, BA is initially a strong inducer of gamma-globin gene expression. However, the level of induction dropped below the level of uninduced cells by the conclusion of the time course. In contrast, IVA and VA produced a lower but sustained induction of reporter gene expression. In order to highlight the differences in the kinetics of gene induction between these compounds, the data shown in FIG. 3 was transformed by normalizing to the fold inductions observed for BA. These results are shown in FIG. 4. This transformation emphasizes that VA and IVA are marginally better inducers than BA at 74 hr and significantly better inducers than BA at 122 hr post induction.

Figure 5:
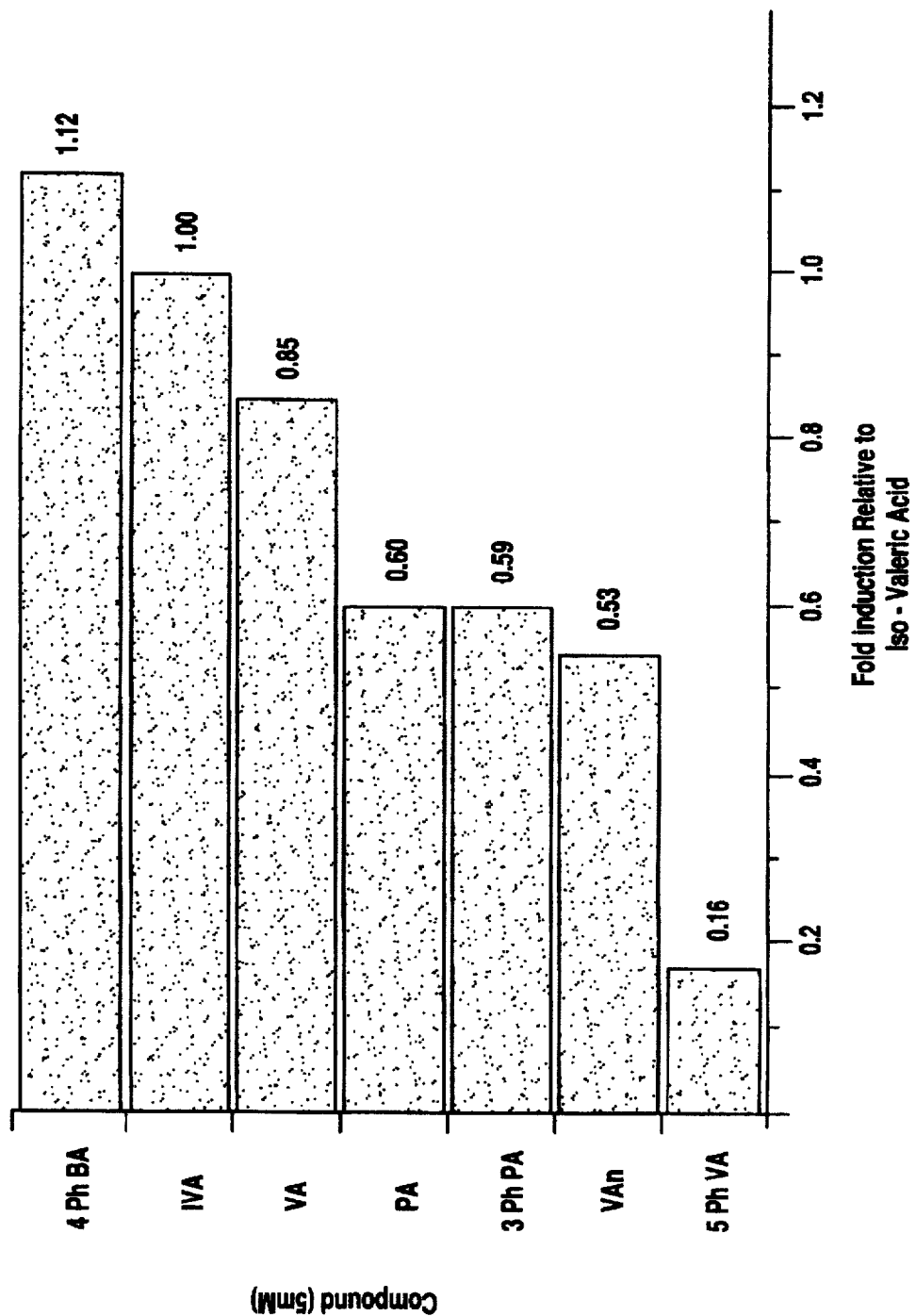
FIG. 5 is a graphic representation of reporter gene activity in K562 cells stably transfected with the gamma3'PE construct upon induction with 4-phenyl butyric acid (4 PH BA), isovaleric acid (IVA), valeric acid (VA), propionic acid (PA), 3-phenyl propionic acid (3 Ph P), valeric acid anhydride (VAn) and 5-phenyl valeric acid (5 PH VA). Fold induction is presented relative to induction by isovaleric acid.
Figure 6:
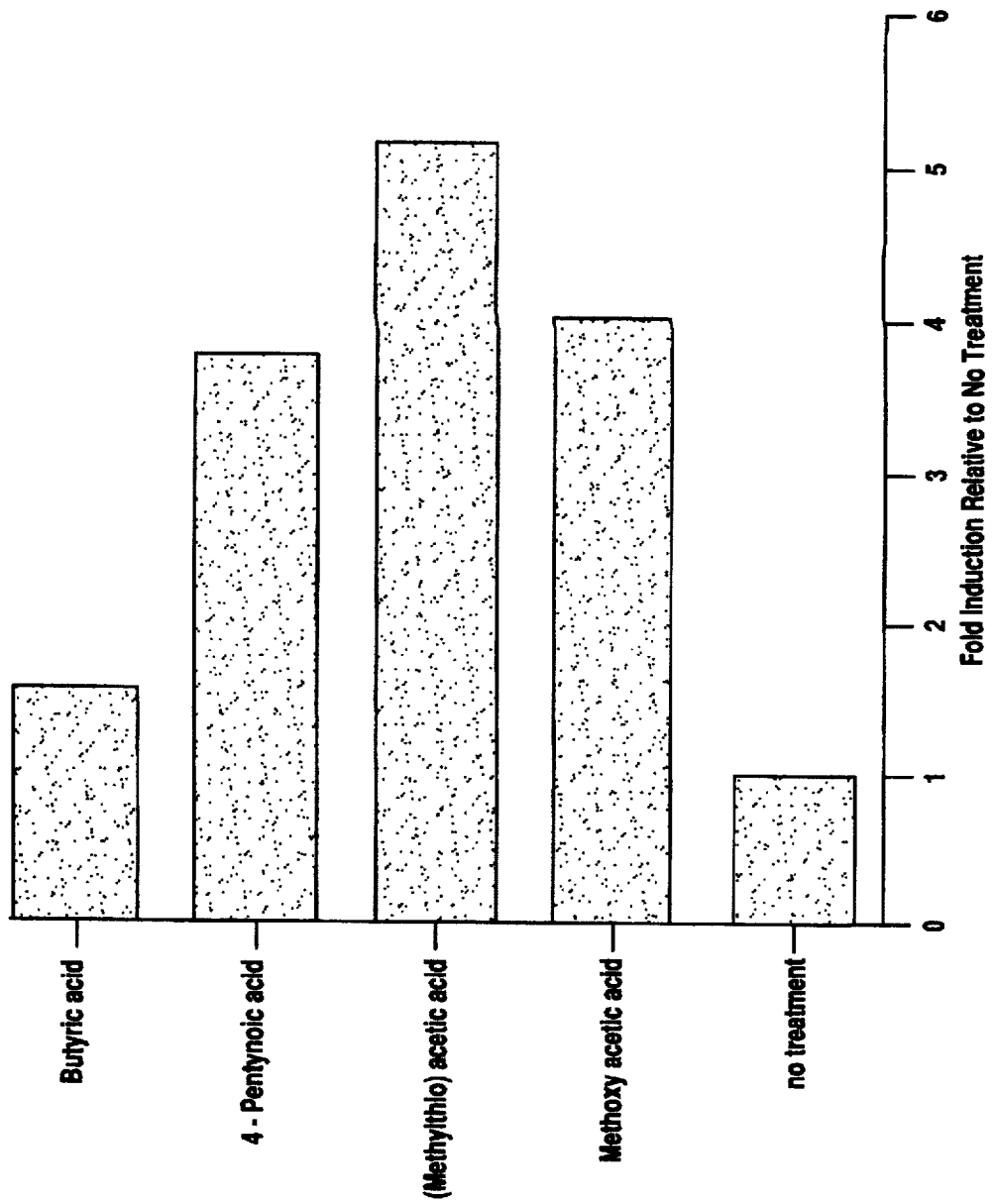
FIG. 6 is a graphic representation of reporter gene activity in K562 cells stably transfected with the gamma3'PE construct upon induction with butyric acid, 4-pentynoic acid, methylthioacetic acid, methoxy acetic acid or without treatment. Fold induction is presented relative to induction in untreated cells.

Using the same gamma globin-reporter gene screening assay described above, other short chain fatty acids, and derivatives thereof, were assayed and shown to be capable of inducing reporter gene activity. Cells were treated with the test compounds (at 5 mM) for 24 hours and luciferase activity in cell supernatants were assayed as described above. The results are shown in FIGS. 5 and 6. FIG. 5 present the induction capability of various phenyl and anhydride derivatives of short chain fatty acids. The data is presented as the fold-induction relative to the activity of isovaleric acid. The results demonstrate that propionic acid (PA), 3-phenyl propionic acid (3 Ph PA), valeric acid anhydride (VAn) and 5-phenyl valeric acid (5 Ph VA) each induce detectable reporter gene activity, although to a lesser extent than VA or IVA. 4-phenyl butyric acid (4 Ph BA) induces detectable reporter gene activity to a slightly greater extent than VA or IVA. FIG. 6 presents the induction capability of various alkynoic and thioether derivatives of short chain fatty acids. Cells were treated with the compounds at 5 mM for 72 hours. The data is presented as the fold induction of reporter gene activity in treated cells as compared to untreated cells. The results demonstrate that 4-pentynoic acid and methoxyacetic acid are capable of inducing reporter gene activity approximately 4-fold and methylthioacetic acid is capable of inducing reporter gene activity approximately 5-fold in this assay system. In contrast, butyric acid was observed to induce reporter gene activity only approximately 2-fold.

EXAMPLE 4

Induction of Gamma Globin and GATA-1 mRNA by Valeric Acid and Isovaleric Acid The gamma globin-reporter gene screening assay described in Example 3 indicated that valeric acid (VA) and isovaleric acid (IVA) can induce gamma globin gene expression. To demonstrate that VA and IVA induce expression of the endogenous gamma globin gene, K562 cells were treated with VA or IVA (5 mM) for 96 hours, total RNA was harvested from the cells and the RNA was analyzed by Northern hybridizations. Total RNA was prepared by the method of McDonald as described in Sambrook et al., (1989) *Molecular Cloning: A Laboratory Manual*, 2nd Edition, Cold Spring Harbor Laboratory Press. 10 µg total cellular RNA was electrophoresed through agarose gels containing 3.3% formaldehyde. The electrophoresed RNA was then transferred to nitrocellulose filters by standard methods. Each sample was hybridized to specific probes for gamma globin mRNA, mRNA encoding the erythroid specific transcription factor GATA-1 and 28S ribosomal RNA (which was used for standardization). The gamma globin and GATA-1 probes were cDNA probes, which were labeled with $^{32}$p by random priming reactions (Promega Biotech Inc.). The 28S ribosomal RNA probe was an oligonucleotide having the sequence 5' TTCACTCGCCGTTACTGAGG-GAATCCTGGTTAG 3' (SEQ ID NO: 3), which was labeled by 5' end labeling using T4 polynucleotide kinase (New England Biolabs). Nucleotide probes were hybridized to the RNA nitrocellulose filters according to standard techniques. After hybridization, radioactive signals on the nitrocellulose filters were directly quantified using a BioRad GS-250 Molecular Imager. mRNA hybridization intensities were normalized to the amount of 28S ribosomal RNA present for each sample. The results are summarized below in Table 1:

TABLE 1

RNA Analysis of VA and IVA Treated K562 Cells

| Treatment | RNA Detected | Raw Value | Normalized Value | Fold Induction |
|---|---|---|---|---|
| No treatment | GATA-1 | $9.19 \times 10^5$ | $5.7 \times 10^4$ | — |
| BA | GATA-1 | $2.23 \times 10^5$ | $5.8 \times 10^4$ | 1 |
| IVA | GATA-1 | $1.47 \times 10^6$ | $1.3 \times 10^6$ | 23 |
| VA | GATA-1 | $3.96 \times 10^5$ | $3.5 \times 10^5$ | 6 |
| No treatment | gamma globin | $1.18 \times 10^7$ | $7.4 \times 10^5$ | — |
| BA | gamma globin | $3.58 \times 10^6$ | $9.4 \times 10^5$ | 1.3 |
| IVA | gamma globin | $5.94 \times 10^6$ | $5.3 \times 10^6$ | 7 |
| VA | gamma globin | $3.35 \times 10^6$ | $3.3 \times 10^6$ | 4.4 |
| No treatment | 28S | $2.83 \times 10^7$ | | |
| BA | 28S | $6.19 \times 10^6$ | | |
| IVA | 28S | $1.85 \times 10^6$ | | |
| VA | 28S | $1.66 \times 10^6$ | | |

The normalized data indicate that cells treated with VA or IVA have a higher steady state level of gamma globin mRNA than untreated cells or cells treated with BA, demonstrating induction of gamma globin gene expression by VA and IVA. Additionally, the data indicate a significant induction of mRNA encoding GATA-1 upon treatment of cells with VA or IVA.

EXAMPLE 5

Viability of Cells Treated with Short Chain Fatty Acids

Figure 7:
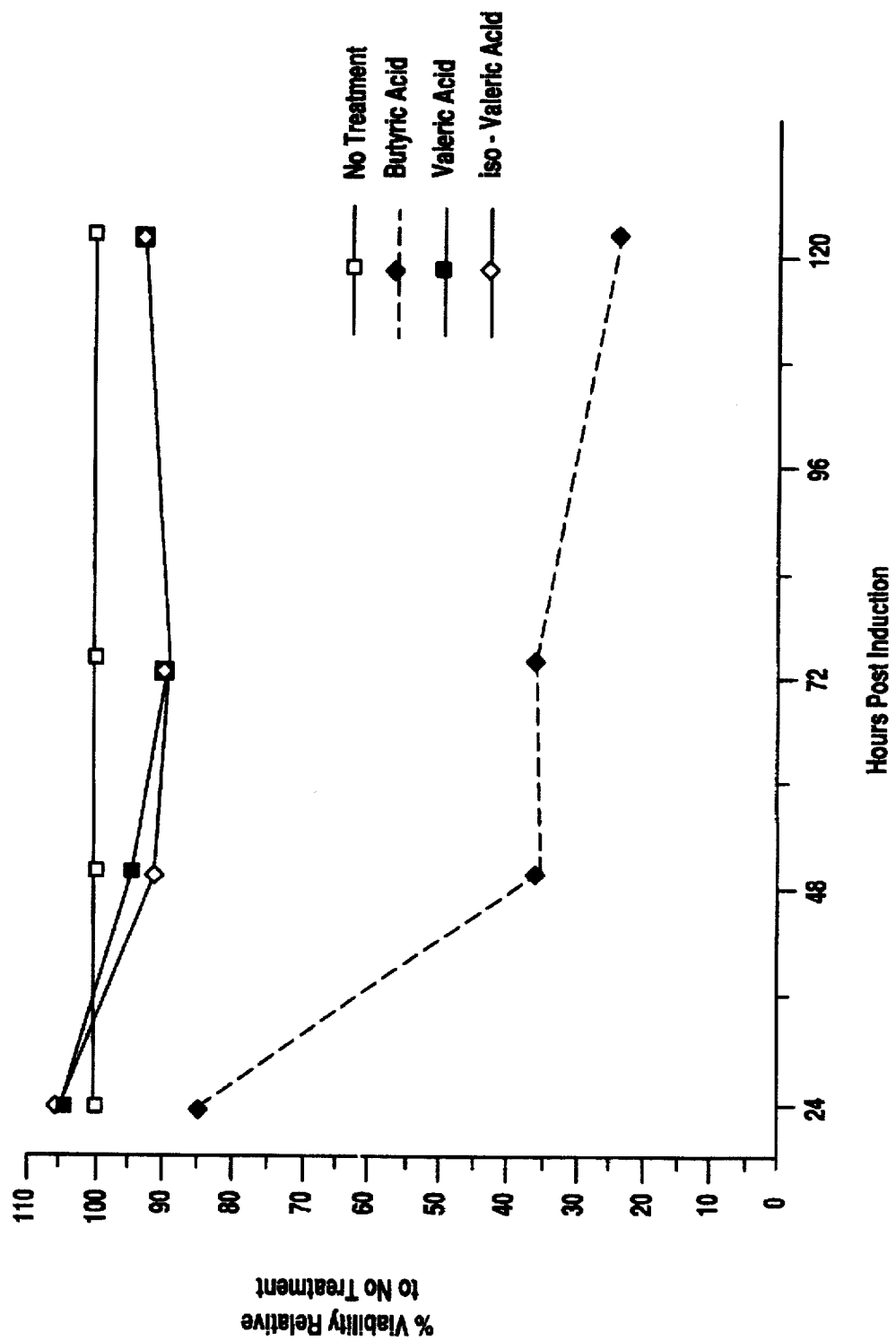
FIG. 7 is a graphic representation of the viability of K562 cells stably transfected with the gamma3'PE reporter gene construct after treatment with butyric acid (BA), valeric acid (VA) or isovaleric acid (IVA).
Figure 8:
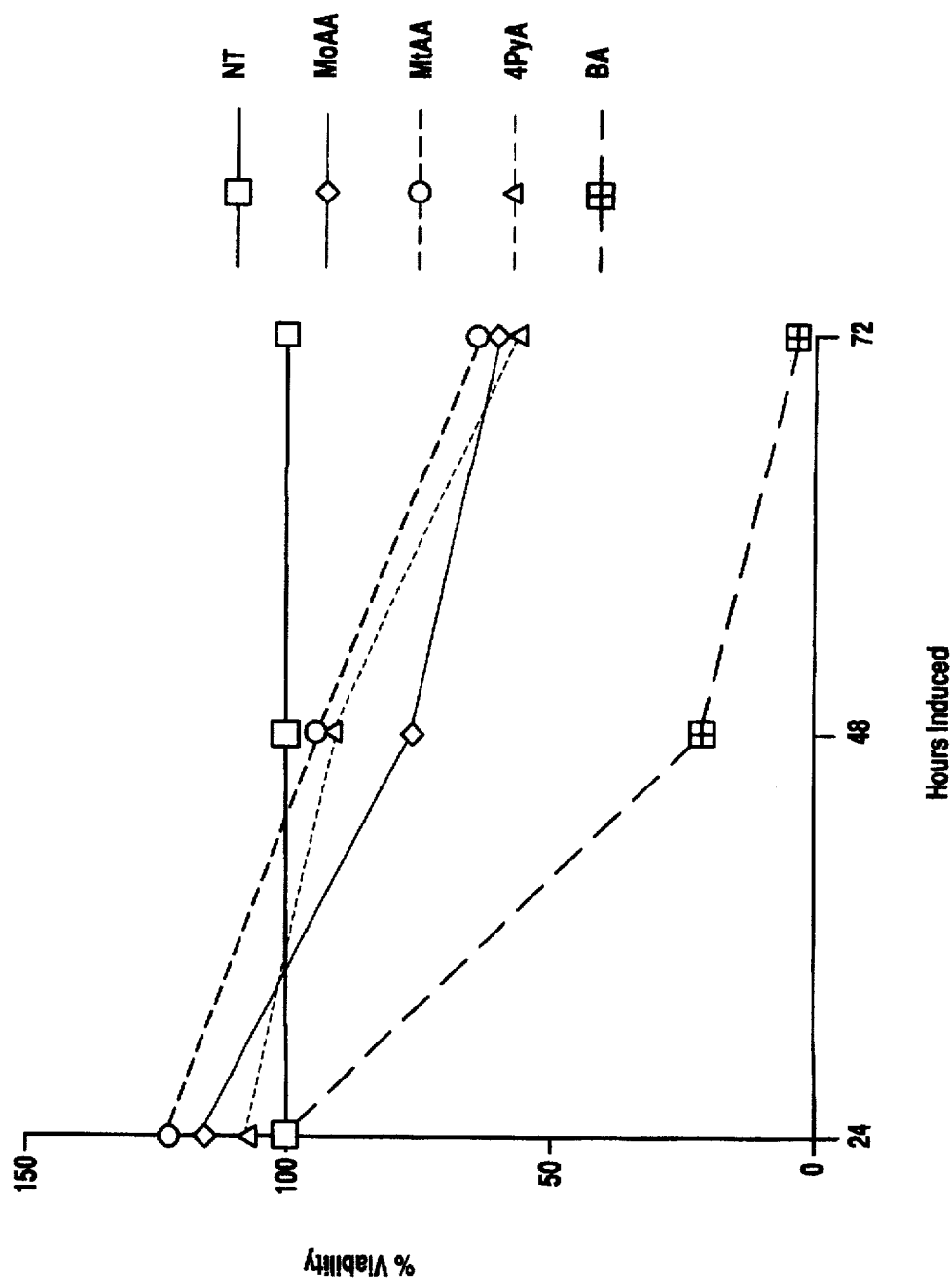
FIG. 8 is a graphic representation of the viability of K562 cells stably transfected with the gamma3'PE reporter gene construct either untreated (NT) or after treatment with butyric acid (BA), methoxyacetic acid (MoAA), methylthioacetic acid (MtAA), 4-pentynoic acid (4PyA).

The cell viability of K562 cells treated with butyric acid (BA), valeric acid (VA), isovaleric acid (IVA), methylthioacetic acid (MtAA), 4-pentynoic acid (4PyA) or methoxyacetic acid (MoAA) was also examined by quantitating cell viability using the MTT assay, described above, at various time points after cell treatment. The results are illustrated graphically in FIGS. 7 and 8. In the experiment shown in FIG. 7, BA was shown to have a negative effect on cell viability within 24 hours after treatment, leading to less than 30% cell viability after 122 hours of treatment. In contrast, the viability of cells treated with VA or IVA was equivalent to that of untreated cells over the course of the experiment (122 hours). In the experiment shown in FIG. 8, BA was nearly 100% toxic to cells treated with the compound for 72 hours, whereas cells with MtAA, 4PyA or MoAA for 72 hours exhibited greater than 50% viability. Thus, gamma globin gene induction by VA, IVA, MtAA, PyA and MoAA is accompanied by significantly less cell death than induction mediated by BA.

EXAMPLE 6

Characterization of Butyric Acid Transport into Erythroid Cells

Figure 9:
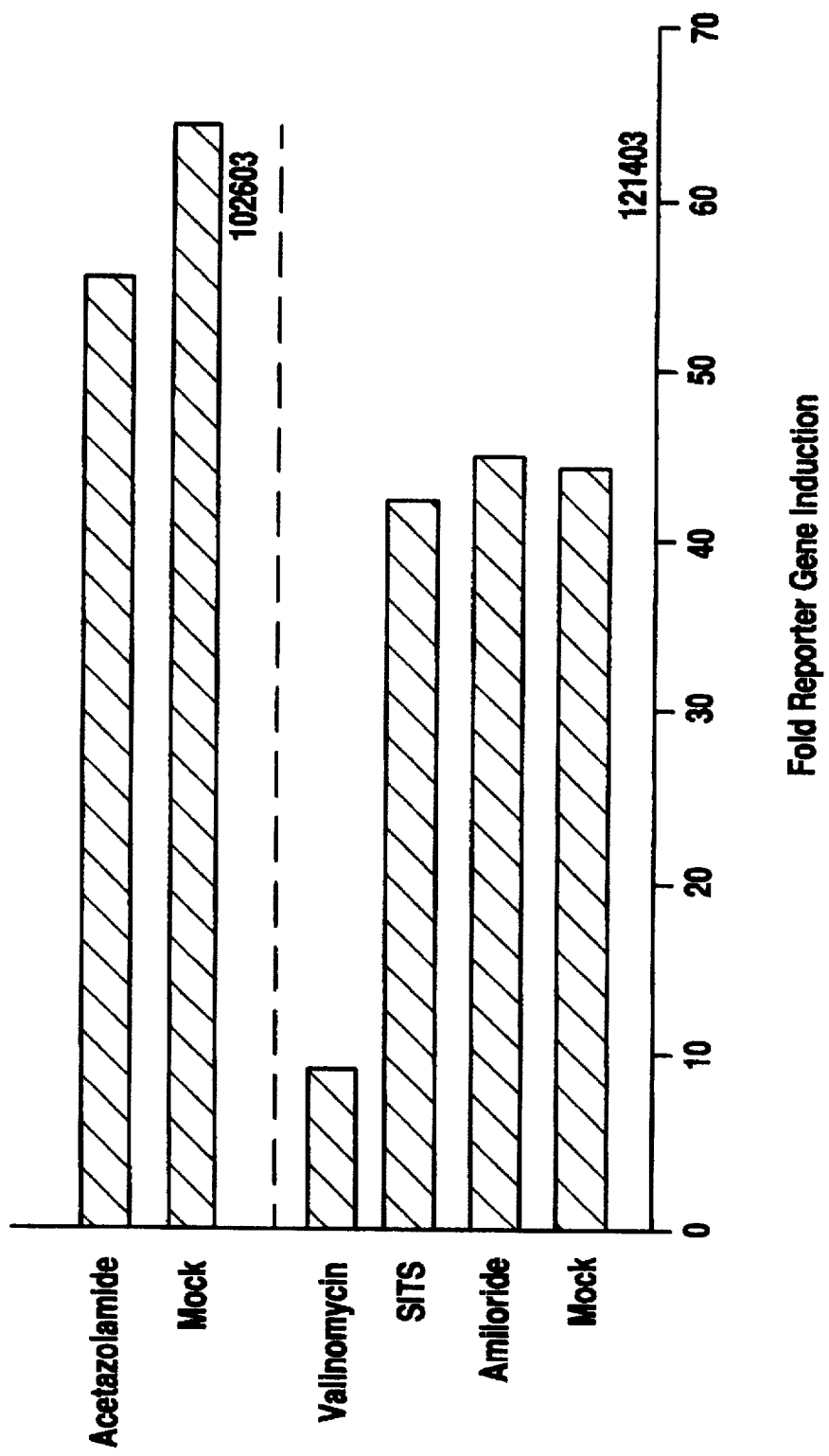
FIG. 9 is a graphic representation of the effect of the potassium ionophore valinomycin on butyric acid-induced reporter gene activity in K562 cells stably transfected with the gamma3'PE reporter gene construct.

To characterize uptake of butyric acid by erythroid cells, K562 cells stably transfected with gamma3'PE were treated with BA in the presence of various transport inhibitors. The inhibitors tested were acetazolamide (1 mM), SITS (10 µM), amiloride (10 µM) and valinomycin (10 mM). Cells were maintained in the continuous presence of both BA and the inhibitor for 24 hours and then luciferase activity in the cells was measured. The results of a representative example of several independent experiments is shown in FIG. 9. While acetazolamide, SITS and amiloride did not affect BA-mediated induction of luciferase activity, treatment of the cells with 10 µM valinomycin resulted in a 4 fold reduction in BA-mediated globin gene induction. Valinomycin specifically affected induction of reporter gene activity and did not affect basal level globin gene expression. Moreover, the effects of valinomycin did not result from a non-specific toxic effect as determined by trypan blue exclusion.

Figure 10:
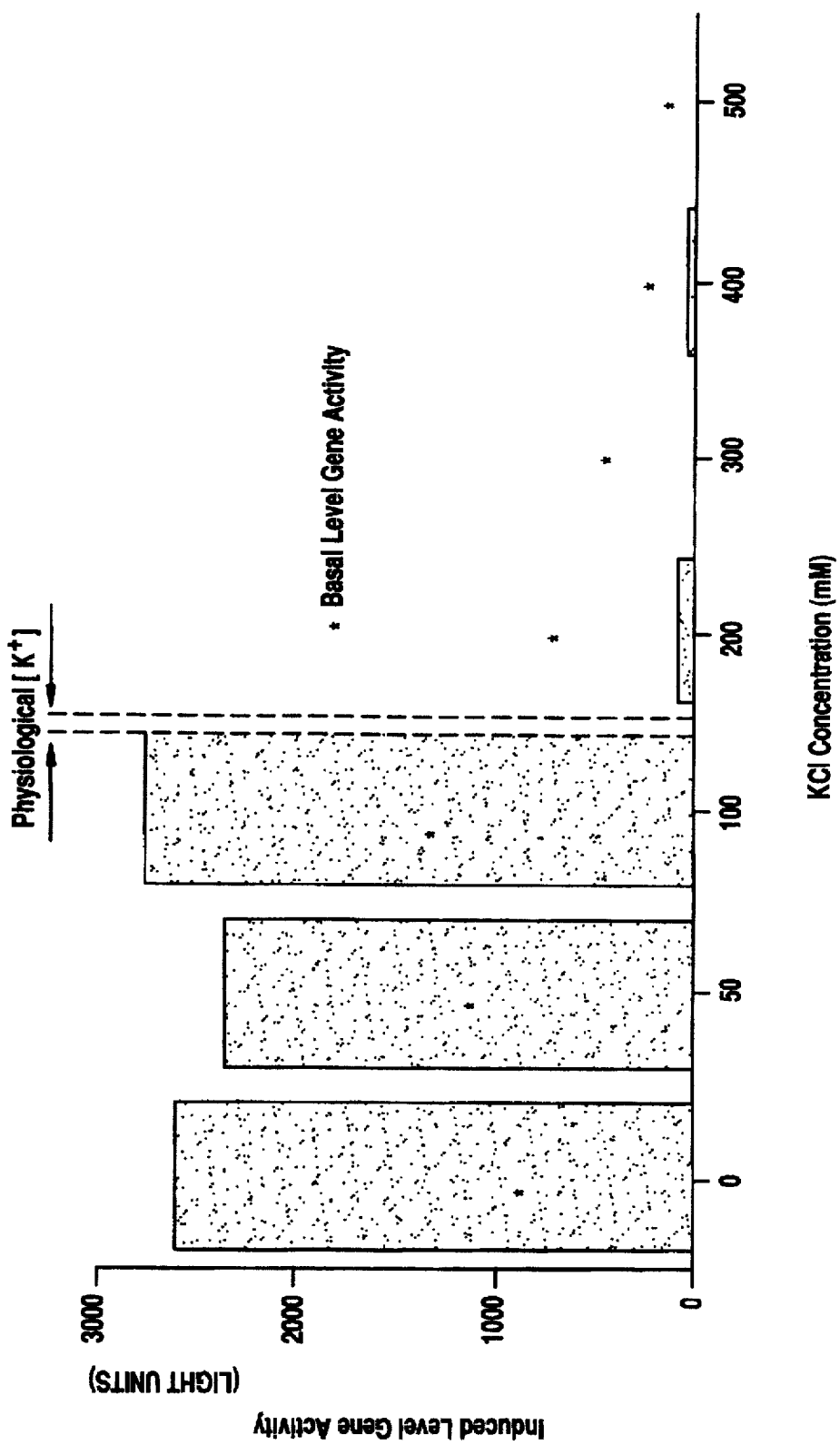
FIG. 10 is a graphic representation of the effect of modulating the K+ gradient across the cell membrane on butyric acid-induced reporter gene activity in K562 cells stably transfected with the gamma3'PE reporter gene construct.

Valinomycin is a potassium ionophore known to cause depolarization of the $K^+$ gradient existing across cell membranes. To determine whether the effect of valinomycin indicated a requirement for a $K^+$ gradient for uptake of BA, gamma3'PE reporter cells were incubated in the presence of culture medium supplemented with increasing concentrations of KCl. Thus, as opposed to valinomycin, this treatment extinguishes the existing $K^+$ gradient from the external side of the membrane without affecting internal $K^+$ concentrations. Cells cultured in increasing concentrations on KCl were treated for 5 hours with BA and then harvested and assayed for luciferase activity. The results are shown in FIG. 10, wherein the bars indicate the level of reporter gene activity after induction in the presence of the indicated concentration of KCl and the asterisks indicate basal (uninduced) levels of reporter gene activity in replicate cultures. The data demonstrate that incubation of cells in increasing concentrations of $K^+$ inhibited BA-induced reporter gene expression at a discrete external concentration of $K^+$ ion (approximately 200 mM). At this concentration of KCl, basal level gene expression was not affected, indicating that loss of induction did not reflect non-specific toxicity of $K^+$ on gene expression (although a reduction in basal level globin expression was observed at higher $K^+$ concentrations). These results, together with the inhibitory effects of valinomycin, are consistent with transport of BA into erythroid cells requiring an intact K+ gradient across the cell membrane.

Figure 11:
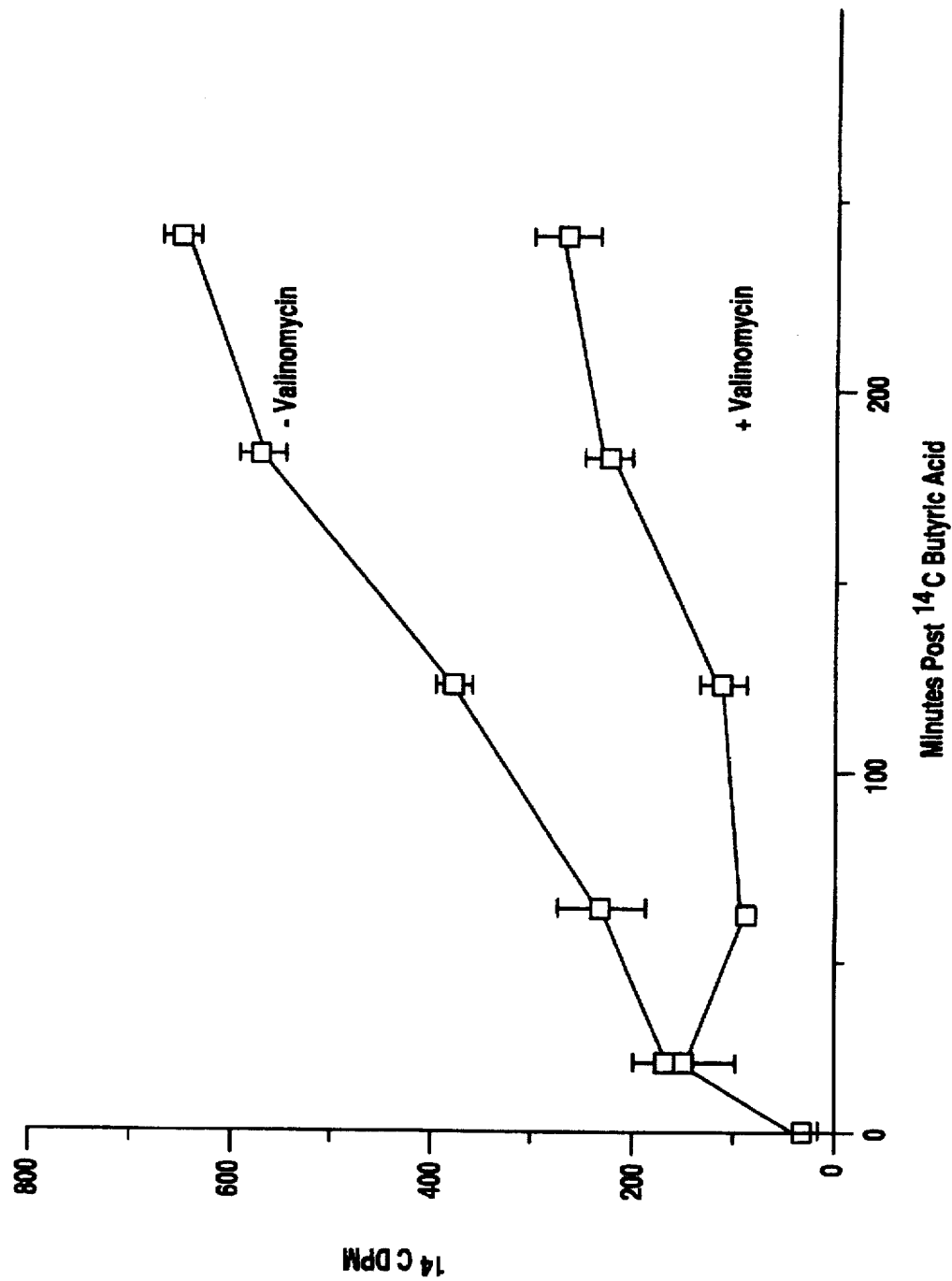
FIG. 11 is a graphic representation of the effect of the potassium ionophore valinomycin on transport of radiolabeled butyric acid into K562 cells.

To directly examine whether transport of BA into erythroid cells required an intact K+ gradient, the incorporation of $^{14}C$ BA into gamma3'PE-transfected K562 cells was assayed in the presence and absence of 10 µM valinomycin. Cells were incubated with 10 µM valinomycin for 1 hour prior to addition of $^{14}C$ butyric acid (obtained commercially from Dupont/New England Nuclear) to a final concentration of 50 µM. At various times after addition of $^{14}C$ BA, cells were harvested by vacuum filtration through a GF/C filter (Whatman) and washed with a total of 5 ml of RPMI culture media. Radioactivity associated with the cells was quantified directly by liquid scintillation counting of the filter. The results, shown in FIG. 11, indicate that the rate of $^{14}C$ BA incorporation into the cells is inhibited nearly three fold by the addition of valinomycin. Although cells treated with valinomycin did accumulate some $^{14}C$ BA, it is not clear whether this was actually internalized or bound to the surface of the cell. Neutralization of the potassium gradient could be expected to selectively prevent internalization but not binding of radioligand. The inhibitory effect of valinomycin on uptake of BA by erythroid cells is in contrast to results reported for BA uptake by colonocytes, which is not inhibited by valinomycin (see Mascolo, N. et al. (1991) *Gastroenterology* 101:331–338). Accordingly, the results described herein are consistent with an erythroid-specific transport mechanism for uptake of BA that is dependent upon an intact $K^+$ gradient across the cell membrane.

EXAMPLE 7

Butyric Acid Induced Signal Transduction in Erythroid Cells

Lack of a Requirement for Protein Synthesis

To determine if BA exerts its inductive effects by acting directly on pre-existing proteins in the cells, the effect of the protein synthesis inhibitor cycloheximide (CHX) on BA-induced expression of RNA was analyzed. In these experiments, gamma3'PE cells were incubated with 150 µg/ml CHX for 2 hr prior to addition of BA (5 mM). Control cells were incubated with either CHX or BA alone or were mock incubated. Cells were harvested 5 hr later for preparation of total RNA. RNA samples were electrophoresed, transferred to nitrocellulose and hybridized to a $^{32}P$-labeled luciferase cDNA probe as described in Example 4. The radioactive signals on the filter were quantitated using a BioRad GS-250 Molecular Imager and mRNA levels were normalized to values obtained for mock treated samples. The results are presented graphically in FIG. 12, Panel A. BA treatment alone increased gamma globin-regulated luciferase mRNA by approximately 6 fold. Cycloheximide treatment alone also resulted in a significant increase in gamma globin-regulated luciferase mRNA, albeit to a lower level than that observed with BA. When cycloheximide and BA were used together, cycloheximide failed to block BA-mediated induction of luciferase mRNA, indicating that with respect to BA induction, gamma globin is an mediate early gene not requiring de novo protein synthesis for induction.

To demonstrate that BA does not induce all genes with mediate early kinetics, the identical Northern blots were reprobed with a $^{32}p$ labeled cDNA probe encoding the transcription factor GATA-1. The results, normalized to mock treated samples, are depicted graphically in FIG. 12, Panel B. In contrast to luciferase mRNA which was induced by BA treatment, the level of GATA-1 RNA decreases about 3 fold in response to BA treatment. However, although the level of GATA-1 mRNA was insensitive to cycloheximide treatment alone, the BA induced decrease in GATA-1 mRNA level was sensitive to cycloheximide treatment (i.e., sensitive to a block in protein synthesis). This result indicates that BA induced the synthesis of a new factor that regulates synthesis or degradation of the GATA-1 message and underscores the fact that the effects of BA on gene expression can be quite diverse.

Role of Protein Kinase C.

Figure 14A:
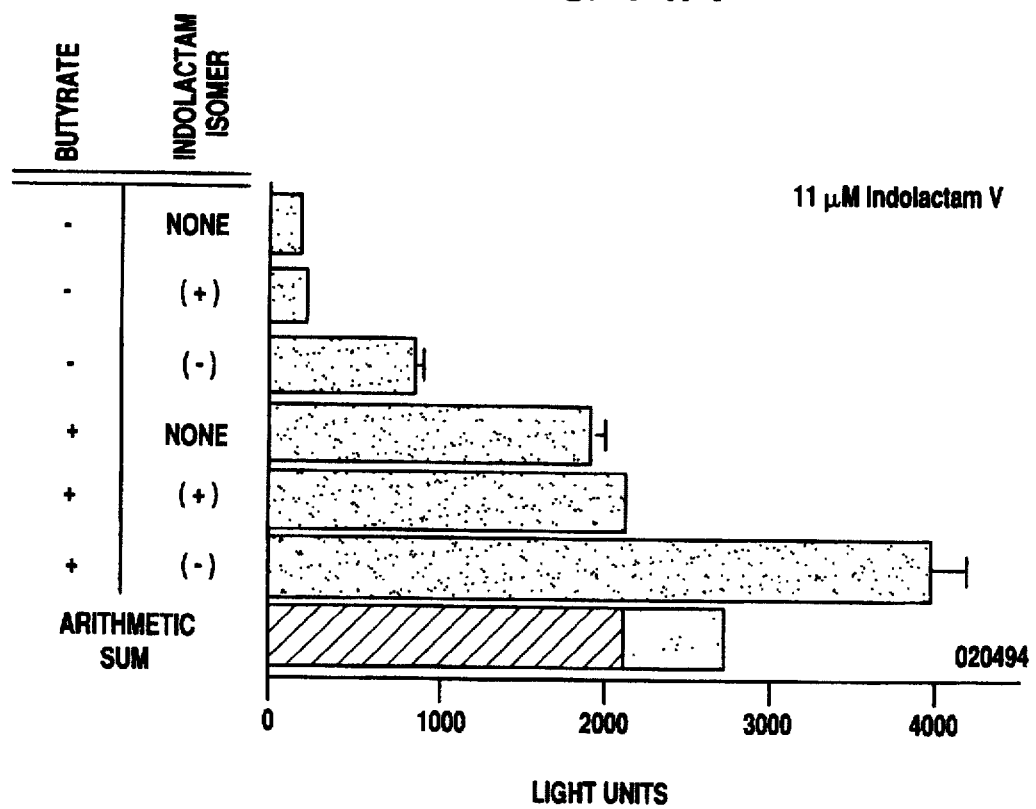
FIGS. 14A–B are graphic representations of the effect of (−) indolactam V or (+)indolactam V on BA-induced reporter gene activity in K562 cells stably transfected with the gamma3'PE reporter gene construct. The indolactam compounds were used at a concentration of 11 µM (Panel A) or 0.4 µM (Panel B).
Figure 14B:
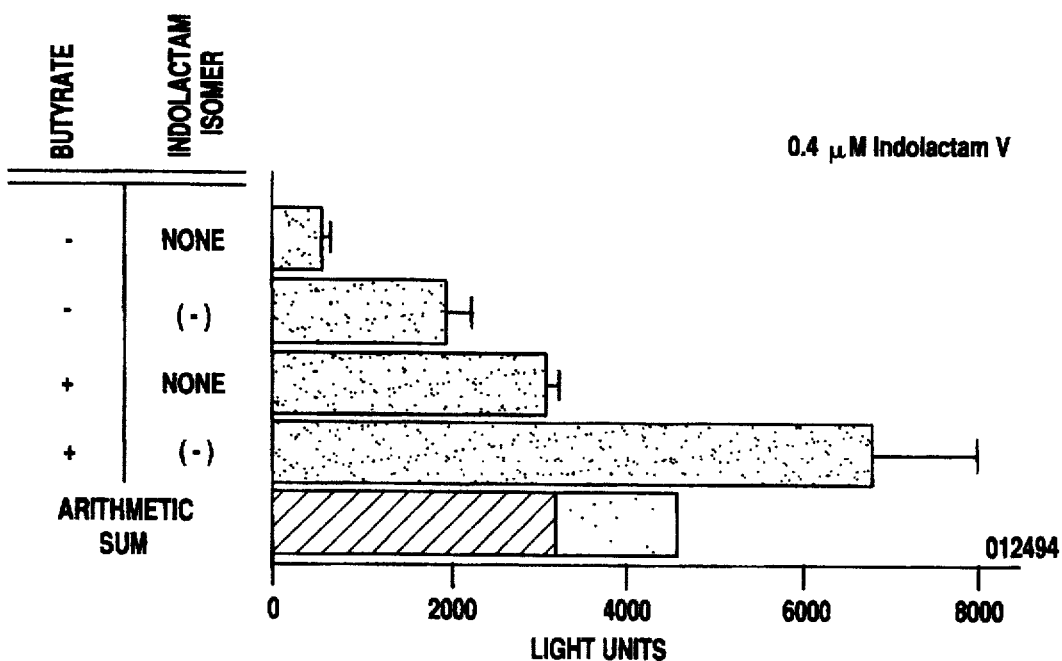

The role of activated protein kinase C (pKC) in the activation of gamma globin gene expression by BA was investigated. In these experiments, the pKC activator (−) indolactam V and its inactive stereoisomer (+) indolactam V were utilized. The chemical structures of these compounds are shown in FIG. 13, panel A and B, respectively. Gamma3'PE cells were pre-incubated with either inducer (at 11 µM or 0.4 µM) or left untreated for 1 hour prior to treatment with 5 mMBA for 24 hours, followed by harvesting of the cells and assaying of luciferase activity. The results are shown in FIG. 14, Panel A (11 µM inducer) and FIG. 14, Panel B (0.4 µM inducer). The data indicate that pKC activation by (−) indolactam V (at either 11 µM or 0.4 µM) had a significant stimulatory effect on basal level globin gene expression, whereas cells treated with the inactive stereoisomer (+) indolactam V were unaffected. Moreover, addition of BA increased globin gene expression in cells treated with (−) or (+) indolactam V and untreated cells by the same fold increment. The net increase in gene expression resulting from combined treatment with both (−) indolactam V and BA was well above the arithmetic sum of the level of induction achieved by either of these compounds separately. Thus, it appears that these compounds act synergistically through pathways converging at some point downstream of the initial site of action of either inducer.

Figure 15:
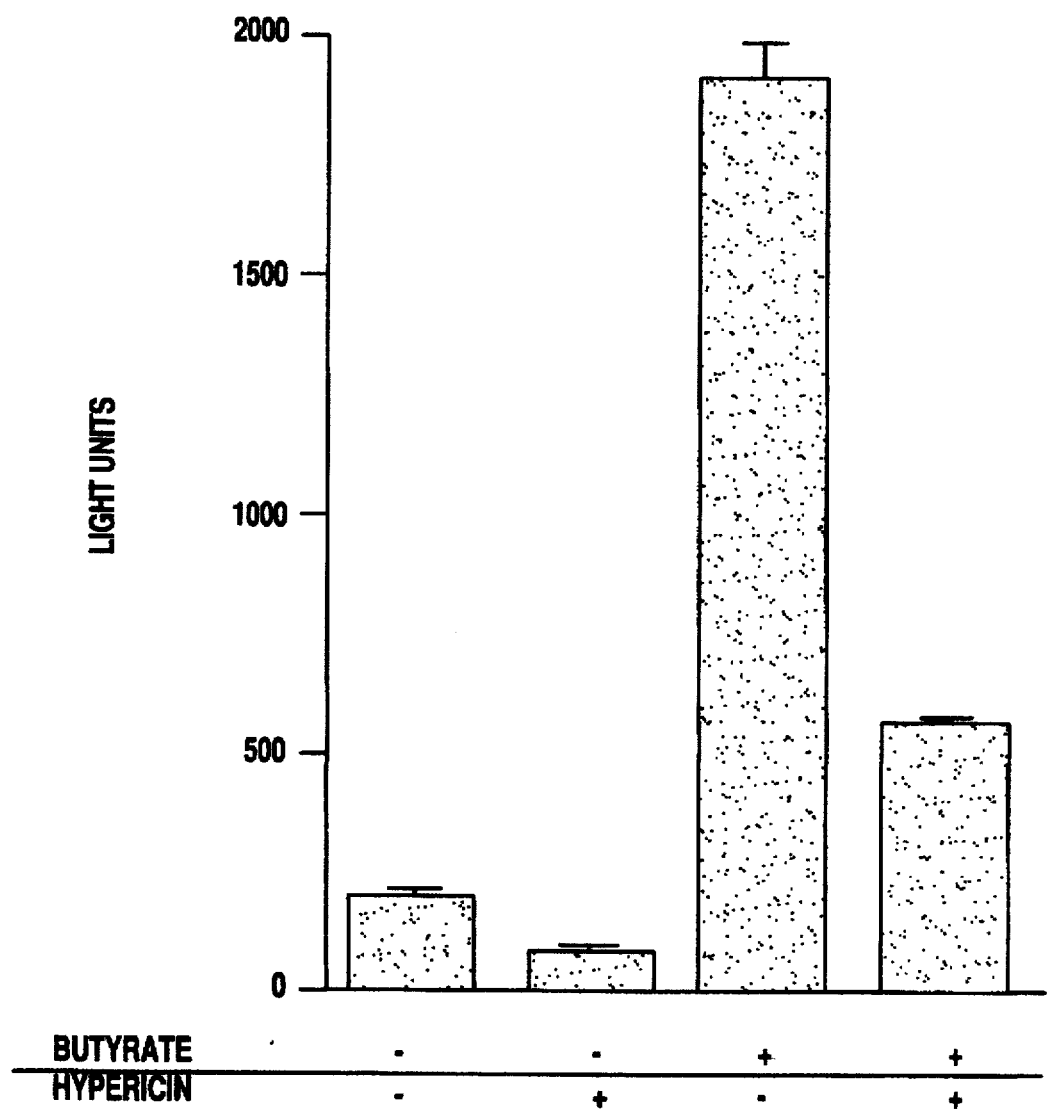
FIG. 15 is a graphic representation of the effect of the protein kinase C inhibitor hypericin on BA-induced reporter gene activity in K562 cells stably transfected with the gamma3'PE reporter gene construct.

Consistent with the results using the pKC activator (−) indolactam V are the results of experiments utilizing the pKC inhibitor hypericin. In these experiments, cells were incubated in the presence or absence of hypericin (10 mM; LC Laboratories) for one hour prior to treatment with 5 mMBA for 24 hours, followed by harvesting of the cells and assaying of luciferase activity. The results, shown in FIG. 15, demonstrate that hypericin leads to a significant reduction in both basal level and BA induced globin gene expression, indicating that inhibiting the basal level of activated pKC in the reporter cell line significantly inhibited the ability of BA to induce gene expression.

The results described above indicate a role for activated protein kinase C in the mechanism of gamma globin gene induction mediated BA. Because there was evidence for synergism when both the pKC and BA pathways were activated, this suggests that these pathways converge to affect a single substrate.

EXAMPLE 8

Mapping of Sequences Necessary for Butyrate Responsiveness of the Gamma Globin Gene Promoter Luciferase reporter gene constructs containing serial deletions in the 5' end of the gamma globin promoter were made by cloning truncated promoter DNA fragments upstream (i.e., 5') of the luciferase gene in pGL2. The gamma globin 3' Proximal Enhancer element (3'PE) was cloned downstream (i.e., 3') of the luciferase reporter gene in these constructs. Truncated gamma globin promoter DNA fragments were generated by PCR using as the upstream primer oligonucleotides having the sequences:

(−1115) ACCAAAAAACCTCGAGAAATACTTCCTA (SEQ ID NO: 4)
(−1009) TAGTGTCTCGAGTATTAGTCAATAAAAA (SEQ ID NO: 5)
(−908) GAAGTGAACCTCGAGTTTATACAAGATA (SEQ ID NO: 6)
(−783) GCACACACACTTCTCGAGTGGTAAATA (SEQ ID NO: 7)
(−667) CGGATAAGTAGATCTCGAGGTAAGCAT (SEQ ID NO: 8)
(−577) CACTGCACTCTCGAGAAATTAAGAGAT (SEQ ID NO: 9)
(−424) TTCACAATCCCTCGAGTTTTCAAAAAT (SEQ ID NO: 10)
(−311) CTCTATGCTCGAGGAAGGAAACTAGCTAAA (SEQ ID NO: 11)
(−179) CCCCACCATATCTCGAGGCAAATATCT (SEQ ID NO: 12)
(−108) GCCTTGCCTTAACCTCGAGCCTTGACAA (SEQ ID NO: 13)

The downstream primer used was an oligonucleotide having the sequence:
(+33) GGACTAGAAGCTTATTGATAACCTCA (SEQ ID NO: 14)

To create a construct with 5' terminus at position −140, the −577 reporter gene construct was digested with NcoI and KpnI, the fragment containing the deleted promoter and reporter gene (i.e., the large restriction fragment) was treated with T4 DNA polymerase to fill-in the restriction sites and the fragment was treated with T4 DNA ligase to religate the construct.

Figure 16:
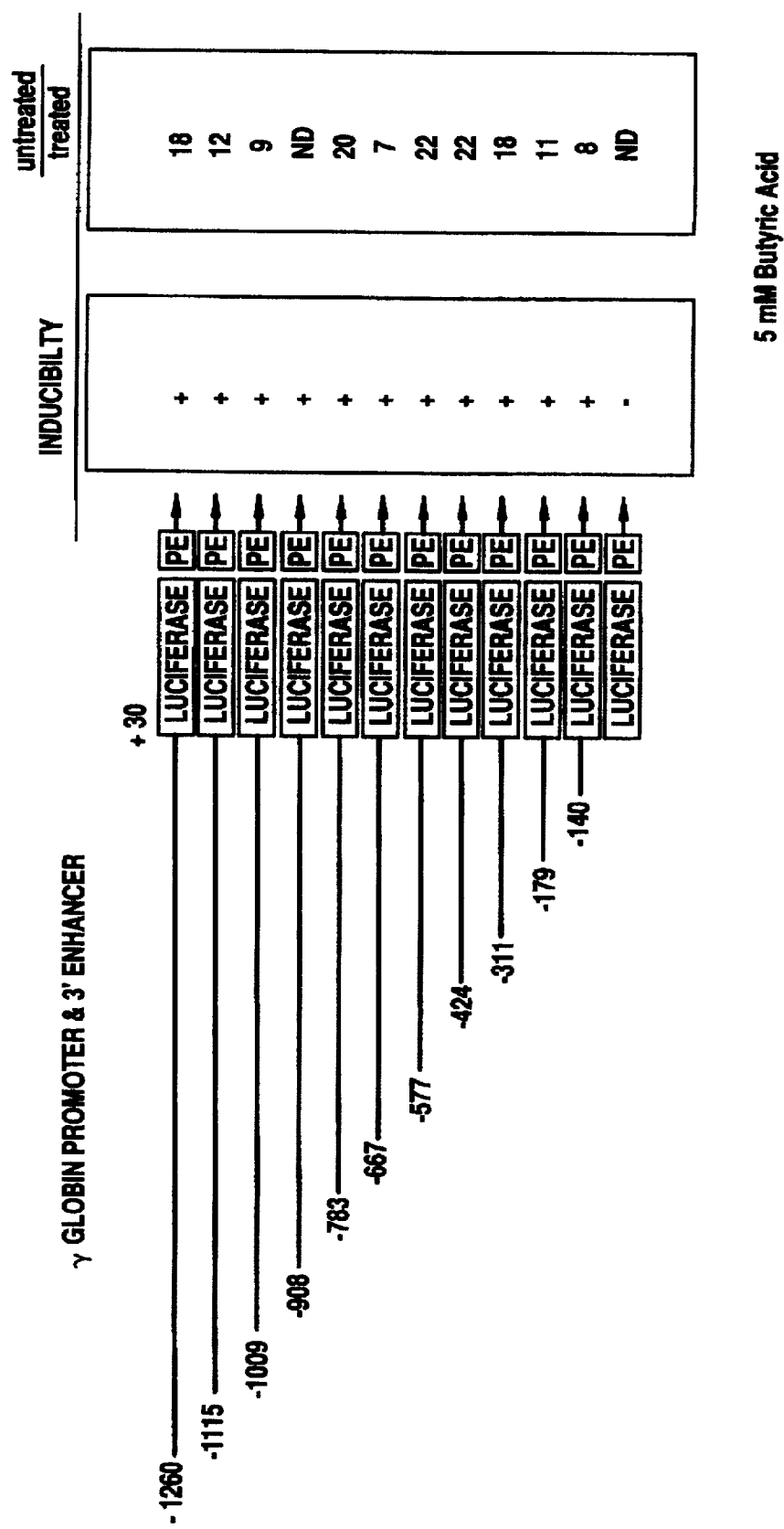
FIG. 16 is a schematic representation of gamma globin promoter deletion constructs, depicting the inducibility of reporter gene activity by butyric acid for each construct.
Figure 17:
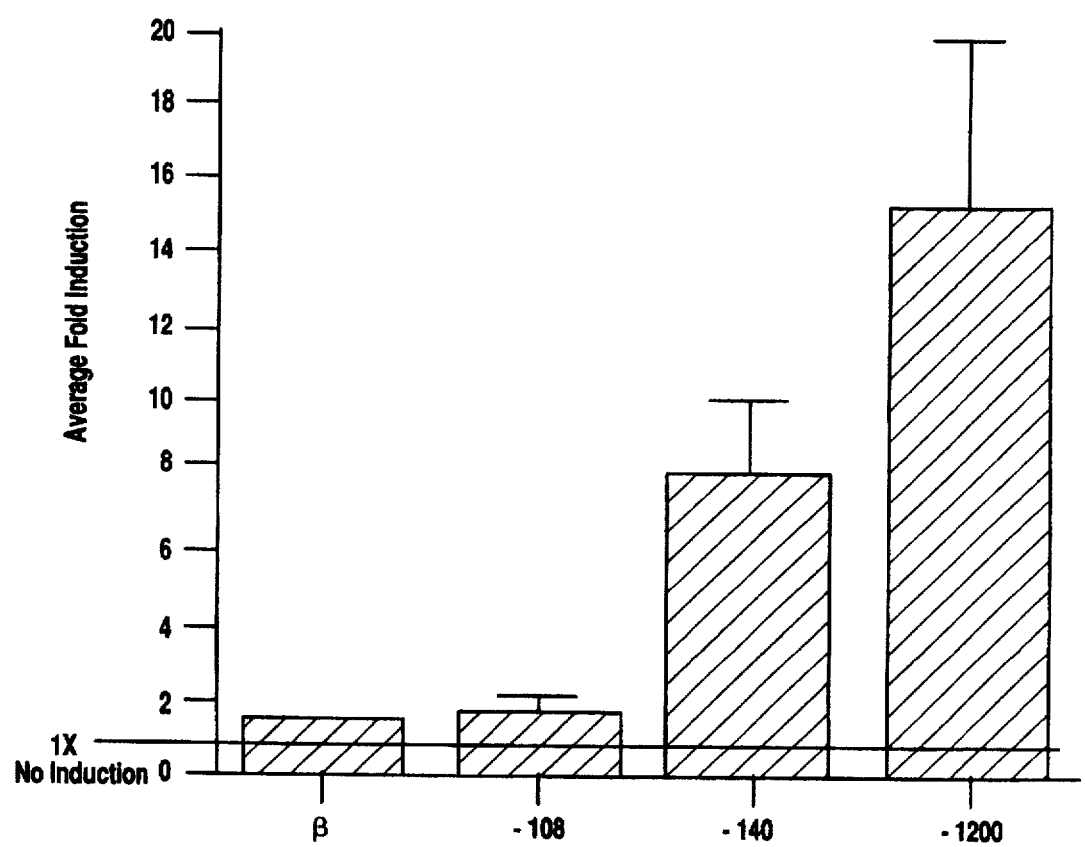
FIG. 17 is a graphic representation of the butyric acid inducibility of reporter gene constructs including the human beta globin promoter (β), the proximal 108 base pairs of the human gamma globin gene promoter (−108), the proximal 140 base pairs of the human gamma globin gene promoter (−140) or 1200 base pairs of the human gamma globin gene promoter (−1200).

To determine the inducibility of each deletion construct by butyric acid, the constructs were introduced into K562 cells by electropotation as described above. Forty-eight hours after transfection, the cells were treated with 5 mMBA. Luciferase activity was measured 24 hours later. The inducibility of the deletion constructs is illustrated in FIGS. 16 and 17. Serial deletion of the gamma globin promoter from position −1260 (relative to the start site of transcription) to −140 did not significantly alter the responsiveness of the reporter construct to BA (see FIG. 16). In contrast, further deletion of the promoter to position −108 markedly reduced the BA inducibility of the construct (see FIG. 17). These results indicate that sequences between positions −140 and −108 of the human gamma globin gene promoter are necessary for responsiveness to butyric acid.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A method for identifying an agent that stimulates gamma globin gene expression in a mammalian cell, comprising:
 a) contacting a mammalian cell with an agent to be tested, wherein a nucleic acid molecule comprising a regulatory region of a gamma globin gene operatively linked to a reporter gene has been introduced into the mammalian cell; and
 b) measuring reporter gene activity in the mammalian cell, wherein an increase in reporter gene activity in the presence of the agent, relative to reporter gene activity in the absence of the agent, is indicative that the agent stimulates gamma globin gene expression.

2. The method of claim 1, wherein the nucleic acid molecule introduced into the mammalian cell comprises a human gamma globin gene promoter operatively linked upstream of the reporter gene.

3. The method of claim 1, wherein the reporter gene encodes a gene product selected from the group consisting of luciferase, chloramphenicol acetyltransferase, alkaline phosphatase and β-galactosidase.

4. The method of claim 1, wherein the mammalian cell is an erythroid cell.

5. The method of claim 4, wherein the mammalian cell is a human erythroleukemia cell.

6. An isolated nucleic acid molecule comprising a human gamma globin gene promoter operatively linked upstream of a reporter gene, wherein the human gamma globin gene promoter has a 5' terminus at position −140 relative to the start site of transcription of the human gamma globin gene, wherein sequences in said nucleic acid molecule upstream of said position −140 are not human gamma globin gene promoter sequences.

7. The nucleic acid molecule of claim 6, wherein the reporter gene encodes a gene product selected from the group consisting of luciferase, chloramphenicol acetyltransferase, alkaline phosphatase and β-galactosidase.

8. A plasmid comprising the nucleic acid molecule of claim 6 or claim 7.

9. A mammalian host cell into which the plasmid of claim 8 has been introduced.

10. The mammalian host cell of claim 9, which is an erythroid cell.

11. The mammalian host cell of claim 9, which is a human erythroleukemia cell.

12. An isolated nucleic acid molecule comprising a human gamma globin gene promoter operatively linked upstream of a reporter gene, wherein the human gamma globin gene promoter has a 5' terminus at position −1200 relative to the start site of transcription of the human gamma globin gene, wherein sequences in said nucleic acid molecule upstream of said position −1200 are not human gamma globin promoter sequences.

13. The nucleic acid molecule of claim 12, wherein the reporter gene encodes a gene product selected from the group consisting of luciferase, chloramphenicol acetyltransferase, alkaline phosphatase and β-galactosidase.

14. A plasmid comprising the nucleic acid molecule of claim 12 or claim 13.

15. A mammalian host cell into which the plasmid of claim 14 has been introduced.

16. The mammalian host cell of claim 15, which is an erythroid cell.

17. The mammalian host cell of claim 15, which is a human erythroleukemia cell.

18. An isolated nucleic acid molecule comprising a human gamma globin gene 3' enhancer operatively linked downstream of a reporter gene.

19. The nucleic acid molecule of claim 18, which further comprises a human gamma globin gene promoter operatively linked upstream of the reporter gene.

20. The nucleic acid molecule of claim 18, wherein the reporter gene encodes a gene product selected from the group consisting of luciferase, chloramphenicol acetyltransferase, alkaline phosphatase and β-galactosidase.

21. A plasmid comprising the nucleic acid molecule of claim 18 or claim 19 or claim 20.

22. A mammalian host cell into which the plasmid of claim 21 has been introduced.

23. The mammalian host cell of claim 22, which is an erythroid cell.

24. The mammalian host cell of claim 22, which is a human erythroleukemia cell.

25. A method for identifying an agent that stimulates gamma globin gene expression in a mammalian cell, comprising:
 a) contacting a mammalian cell with an agent to be tested, wherein a nucleic acid molecule comprising a human gamma globin gene 3' enhancer operatively linked downstream of a reporter gene has been introduced into the mammalian cell; and
 b) measuring reporter gene activity in the mammalian cell, wherein an increase in reporter gene activity in the presence of the agent, relative to reporter gene activity in the absence of the agent, is indicative that the agent stimulates gamma globin gene expression.

26. The method of claim 25, wherein the nucleic acid molecule further comprises a human gamma globin gene promoter operatively linked upstream of the reporter gene.

27. The method of claim 25, wherein the reporter gene encodes a gene product selected from the group consisting of luciferase, chloramphenicol acetyltransferase, alkaline phosphatase and β-galactosidase.

28. The method of claim 25, wherein the mammalian cell is an erythroid cell.

29. The method of claim 25, wherein the mammalian cell is a human erythroleukemia cell.

30. The method of claim 25, wherein reporter gene activity is measured by assaying the enzymatic activity of the gene product encoded by the reporter gene.

31. A method for identifying an agent that enhances stimulation of gamma globin gene expression by a short chain fatty acid, comprising:
   a) contacting a mammalian cell with an agent to be tested and with a short chain fatty acid, wherein a nucleic acid molecule comprising a regulatory region of a gamma globin gene operatively linked to a reporter gene has been introduced into the mammalian cell; and
   b) measuring reporter gene activity in the mammalian cell, wherein an increase in reporter gene activity in the presence of the agent, relative to reporter gene activity in the absence of the agent, is indicative that the agent enhances stimulation of gamma globin gene expression by a short chain fatty acid.

32. The method of claim 31, wherein the short chain fatty acid is selected from the group consisting of butyric acid, valeric acid, isovaleric acid, 4-pentynoic acid, methylthioacetic acid and salts thereof.

33. The method of claim 31, wherein the reporter gene encodes a gene product selected from the group consisting of luciferase, chloramphenicol acetyltransferase, alkaline phosphatase and β-galactosidase.

34. The method of claim 31, wherein the mammalian cell is an erythroid cell.

35. The method of claim 31, wherein the mammalian cell is a human erythroleukemia cell.

36. The method of claim 31, wherein reporter gene activity is measured by assaying the enzymatic activity of the gene product encoded by the reporter gene.

37. The method of claim 1, wherein reporter gene activity is measured by assaying the enzymatic activity of the gene product encoded by the reporter gene.

* * * * *